United States Patent
Chu et al.

(10) Patent No.: US 7,304,122 B2
(45) Date of Patent: Dec. 4, 2007

(54) ELASTOMERIC FUNCTIONAL BIODEGRADABLE COPOLYESTER AMIDES AND COPOLYESTER URETHANES

(75) Inventors: Chih-Chang Chu, Ithaca, NY (US); Ramaz Katsarava, Tbilisi (GE)

(73) Assignee: Cornell Research Foundation, Inc., Ithaca, NY (US)

( * ) Notice: Subject to any disclaimer, the term of this patent is extended or adjusted under 35 U.S.C. 154(b) by 312 days.

(21) Appl. No.: 10/362,848

(22) PCT Filed: Aug. 30, 2001

(86) PCT No.: PCT/US01/27288

§ 371 (c)(1),
(2), (4) Date: Oct. 14, 2003

(87) PCT Pub. No.: WO02/18477

PCT Pub. Date: Mar. 7, 2002

(65) Prior Publication Data

US 2004/0063606 A1    Apr. 1, 2004

(51) Int. Cl.
*C08G 63/02* (2006.01)
*C08G 18/80* (2006.01)
*A61K 9/16* (2006.01)

(52) U.S. Cl. .................. 528/272; 528/176; 528/179; 528/182; 528/184; 528/189; 528/332; 528/335; 528/336; 524/86; 524/233; 424/426; 424/451; 424/457; 424/489; 424/490; 424/497

(58) Field of Classification Search ............... 528/176, 528/179, 182, 184, 189, 332, 335, 336, 339; 524/86, 233; 424/426, 451, 457, 489, 490, 424/497

See application file for complete search history.

(56) References Cited

U.S. PATENT DOCUMENTS

| | | | |
|---|---|---|---|
| 5,100,992 A | 3/1992 | Cohn et al. | 424/501 |
| 5,133,742 A | 7/1992 | Pinchuk | 623/1 |
| 5,485,496 A | 1/1996 | Lee et al. | 378/64 |
| 5,516,881 A | 5/1996 | Lee et al. | 528/320 |
| 5,610,241 A | 3/1997 | Lee et al. | 525/411 |
| 5,721,131 A | 2/1998 | Rudolph et al. | 435/240.243 |
| 5,919,893 A | 7/1999 | Roby et al. | 525/411 |
| 2007/0027293 A1 | 2/2007 | Chu et al. | |

FOREIGN PATENT DOCUMENTS

| | | |
|---|---|---|
| DE | 4224401 A1 | 1/1994 |
| DE | 4224401 | 1/1998 |
| EP | 0396429 A2 | 11/1990 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO-0396429 | 11/1990 |
| WO | WO-98/32398 | 7/1998 |

OTHER PUBLICATIONS

Katsarava, R., et al., "Amino Acid-Baed Bioanalogous Polymers".
Saotome, Y., et al., "Novel Enzymatically Degradable Polymers Comprising a-Amino Acid, 1,2-Ethanediol, and Adipic Acid", *Chemistry Letters*, (1991), pp. 21-24.

*Primary Examiner*—James Seidleck
*Assistant Examiner*—Gennadly Mesh
(74) *Attorney, Agent, or Firm*—Schwegman, Lundberg & Woessner, P.A.

(57) ABSTRACT

The present invention provides elastomeric copolyester amides, elastomeric copolyester urethanes, and methods for making the same. The polymers that are based on α-amino acids and possess suitable physical, chemical and biodegradation properties. The polymers are useful as carriers of drugs or other bioactive substances. The polymers can be linked, intermixed, or a combination thereof, to one or more drugs.

54 Claims, 1 Drawing Sheet

ELASTOMERIC FUNCTIONAL BIODEGRADABLE COPOLYESTER AMIDES AND COPOLYESTER URETHANES

RELATED APPLICATIONS

This application is a 35 U.S.C. 371 of PCT/US01/27288, filed 30 Aug. 2001 and published WO 02/18477 on 7 Mar. 2002, which claims priority from U.S. patent application Ser. No. 09/651,338, filed Aug 30, 2000, now U.S. Pat. No. 6,503,538, which applications and publication are incorporated herein by reference.

BACKGROUND OF THE INVENTION

While they potentially offer many advantages due to their "organic nature," conventional poly(α-amino acids) possess many undesirable physical, chemical and biodegradation properties. For example, the biological and material properties of conventional poly(α-amino acids) cannot be varied over a wide range. In addition, the synthesis of many conventional poly(α-amino acids) is difficult and expensive.

A considerable amount of attention has therefore been focused on replacing the amide (peptide) linkage in the conventional poly(α-amino acids) with a variety of non-amide bonds to provide novel polymeric systems that are based on α-amino acids. One class of α-amino acid derived polymers are polyisopeptides (alternatively known as pseudo-poly(amino acids)), which belong to the XY-type heterochain polymers. Polyisopeptides are usually formed by linking trifunctional α-amino acids in the backbone chains. However, relatively few attempts have been made to synthesize polyisopeptides. For example, Sekiguchi et al. obtained poly-β-(α-alkyl-L-aspartate) by the ring-opening polymerization of β-lactams. See, Rodriguez-Galan, A. et al., *Makromol. Chem., Macromol. Symp.*, 6, 277 (1986) and Vives, J. et al., *Makromol. Chem., Rapid Commun.*, 10(1):13 (1989). One major limiting feature of polyisopeptides is that structural modifications are limited solely to chemical variations at the N-acyl residue of the polyisopeptide. This narrow range of chemical modification has resulted in an undesirably narrow range of material properties of these polymers.

Another class of α-amino acid derived polymers are amino acid based bioanalagous polymers (AABBPs), which belong to the XX-YY heterochain polymers. AABBPs are mainly obtained by the polycondensation of XX (one type of monomer having two X functional groups) and YY (another type of monomer having two Y functional groups). AABBPs are not pure polyamino acids or pseudo-polyamino acids because they include residues of other types of monomers (e.g., dicarboxylic acids and diols).

One class of AABBPs are poly(ester ureas) (PEUs), which are prepared from bis-α-aminoacyl diol monomers. The first attempt to use bis-α-aminoacyl(phenylalanyl) diol for preparing bioabsorbable, semi-physiological polymers similar to poly(ester urea) was by Huang et al. Huang S. J., et al., *J. Appl. Polym. Sci.*, 23(2): 429 (1979). Only low-molecular-weight PEUs, having limited material properties, could be prepared by this route.

Lipatova et al. have also synthesized semi-physiological poly(ester urethane ureas) from bis-L-phenylalanyl diols, diols, and diisocyanates. Lipatova T. E., et al., *Dokl. Akad. Nauk SSSR*, 251(2): 368 (1980) and Gladyr I. I., et al. *Vysokomol. Soed.*, 31B(3): 196 (1989). However, no information on the synthesis of the starting material (e.g., α-diamino diesters) was given.

Yoneyama et al. reported on the synthesis of high-molecular-weight semi-physiological PEUs by the interaction of free α-diamino-diesters with non-physiological diisocyanates. Yoneyama M., et al., *Polym. Prepr. Jpn.*, 43(1): 177 (1994). Contrary to Huang et al. (Huang S. J., et al., *J. Appl. Polym. Sci.*, 23(2): 429 (1979)), high-molecular-weight PEUs were obtained in some cases. In view of this preliminary data, there remains an ongoing need for novel polymers based on α-amino acids that possess a wide range of physical, chemical and biodegradation properties.

SUMMARY OF THE INVENTION

The present invention provides polymers that are based on α-amino acids. In contrast to conventional poly(α-amino acids), the polymers of the present invention (e.g., elastomeric functional copolyester amides and copolyester urethanes) possess advantageous physical, chemical and biodegradation properties. For example, the polymers of the present invention possess suitable biodegradation (weight loss percent) properties under varying conditions, (see, Table III). The hydrolysis of the polymers can be catalyzed by hydrolases (e.g., trypsin, α-chymotrypsin, lipase, etc.). As such, the polymers can be used as carriers for covalent immobilization (attachment) of various drugs and other bioactive substances. In addition, the enzyme catalyzed biodegradation rates of the polymer of the present invention can be changed by varying the polymer composition (e.g., l/p ratio) and/or the nature of the functional groups (e.g., dicarboxylic acids, diols, or α-amino acids).

The present invention provides a polymer of formula (VII):

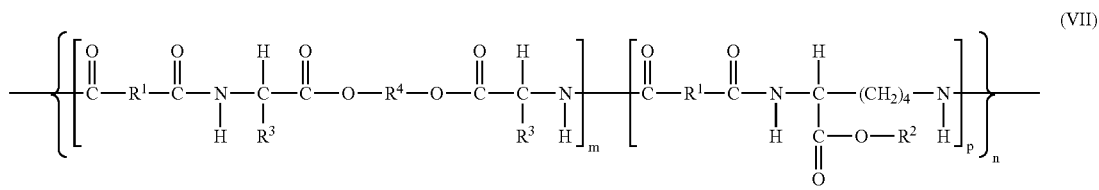

wherein
m is about 0.1 to about 0.9;
p is about 0.9 to about 0.1;
n is about 50 to about 150;
each $R^1$ is independently $(C_2-C_{20})$alkylene;
each $R^2$ is independently hydrogen, or $(C_6-C_{10})$aryl$(C_1-C_6)$alkyl;
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and
each $R^4$ is independently $(C_2-C_{20})$alkylene;

comprising one or more subunits of the formula (1):

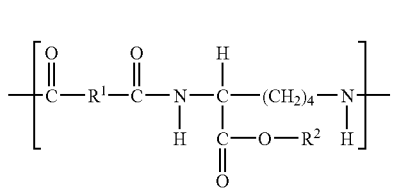

and one or more subunits of the formula (II):

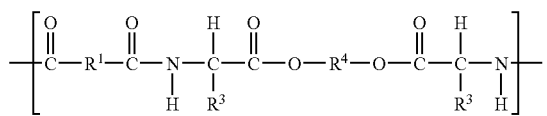

wherein
the combined number of subunits (I) and (II) is about 50 to about 150.

Specifically, each $R^1$ can independently be $(CH_2)_4$, $(CH_2)_8$, or $(CH_2)_{12}$; $R^2$ can independently be hydrogen or benzyl; each $R^3$ can independently be iso-butyl or benzyl; and $R^4$ can independently be $(CH_2)_4$, $(CH_2)_6$, $(CH_2)_8$, or $(CH_2)_{12}$.

The present invention also provides a polymer of formula (VII):

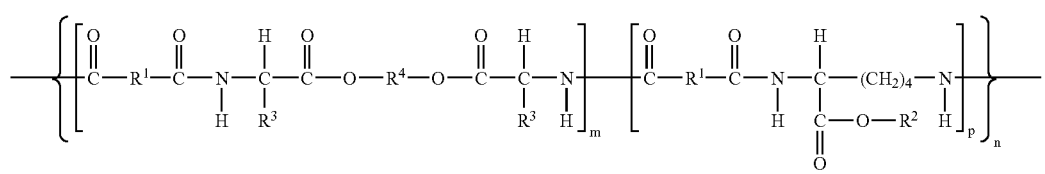

wherein
m is about 0.1 to about 0.9;
p is about 0.9 to about 0.1;
n is about 50 to about 150;
each $R^1$ is independently $(C_2-C_{20})$alkylene;
each $R^2$ is independently hydrogen, or $(C_6-C_{10})$aryl$(C_1-C_6)$alkyl;
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and
each $R^4$ is independently $(C_2-C_{20})$alkylene.

Specifically, each $R^1$ can independently be $(CH_2)_4$, $(CH_2)_8$, or $(CH_2)_{12}$; each $R^2$ can independently be hydrogen or benzyl; each $R^3$ can independently be iso-butyl or benzyl; each $R^4$ can independently be $(CH_2)_4$, $(CH_2)_6$, $(CH_2)_8$, or $(CH_2)_{12}$; p/(p+m) can be about 0.9 to about 0.1; and m/(p+m) can be about 0.1 to about 0.9.

The present invention also provides a polymer of formula (VII) formed from an amount of one or more compounds of formula (III):

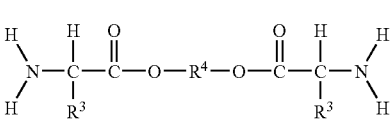

wherein
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and
$R^4$ is independently $(C_2-C_{20})$alkylene; or a suitable salt thereof; and an amount of one or more compounds of formula (IV):

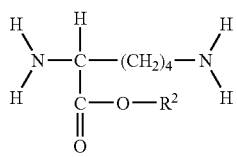

wherein
$R^2$ is independently hydrogen, or $(C_6-C_{10})$aryl$(C_1-C_6)$alkyl; or a suitable salt thereof; and an amount of one or more compounds of formula (V):

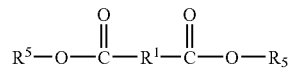

wherein
$R^1$ is independently $(C_2-C_{20})$alkylene; and
each $R^5$ is independently $(C_6-C_{10})$aryl, optionally substituted with one or more nitro, cyano, halo, trifluoromethyl, or trifluoromethoxy.

Specifically, $R^1$ can independently be $(CH_2)_4$, $(CH_2)_8$, or $(CH_2)_{12}$; $R^2$ can independently be hydrogen or benzyl; each $R^3$ can independently be isobutyl or benzyl; $R^4$ can independently be $(CH_2)_4$, $(CH_2)_6$, $(CH_2)_8$, or $(CH_2)_{12}$; each $R^5$ can independently be p-nitrophenyl; the compound of formula (III) can be the di-p-tolunesulfonic acid salt of a bis-(L-α-amino acid)-α,ω-alkylene diester; the compound of formula (IV) can be the di-p-tolunesulfonic acid salt of L-lysine benzyl ester, and the compound of formula (V) can be di-p-nitrophenyl adipate, di-p-nitrophenyl sebacinate, or di-p-nitrophenyl dodecyldicarboxylate.

The present invention also provides a method for preparing a polymer of formula (VII):

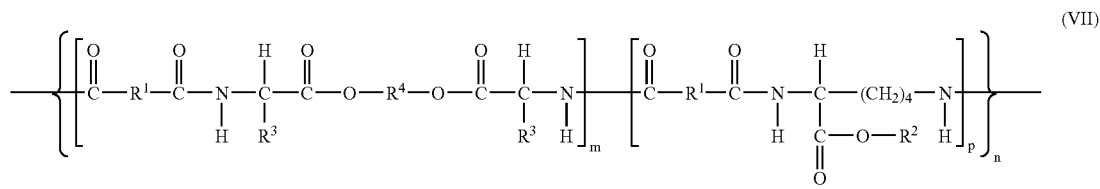

wherein
m is about 0.1 to about 0.9;
p is about 0.9 to about 0.1;
n is about 50 to about 150;
each $R^1$ is independently $(C_2-C_{20})$alkylene;
each $R^2$ is independently hydrogen, or $(C_6-C_{10})$aryl$(C_1-C_6)$alkyl;
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and
each $R^4$ is independently $(C_2-C_{20})$alkylene;

comprising contacting an amount of one or more compounds of formula (III):

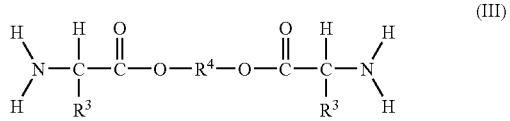

or a suitable salt thereof; and
an amount of one or more compounds of formula (IV):

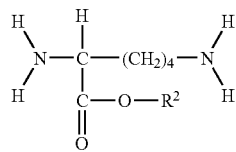

or a suitable salt thereof; and
an amount of one or more compounds of formula (V):

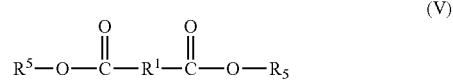

wherein
each $R^5$ is independently $(C_6-C_{10})$aryl optionally substituted with one or more nitro, cyano, halo, trifluoromethyl, or trifluoromethoxy;
under suitable conditions to provide the polymer of formula (VII).

Specifically, each $R^1$ can independently be $(CH_2)_4$, $(CH_2)_8$, or $(CH_2)_{12}$; each $R^2$ can independently be hydrogen or benzyl; each $R^3$ can independently be iso-butyl or benzyl; each $R^4$ can independently be $(CH_2)_4$, $(CH_2)_6$, $(CH_2)_8$, or $(CH_2)_{12}$; each $R^5$ can be p-nitrophenyl; the compound of formula (III) can be the di-p-tolunesulfonic acid salt of a bis-(L-α-amino acid)-α,ω-alkylene diester; the compound of formula (IV) can be the di-p-tolunesulfonic acid salt of L-lysine benzyl ester, the compound of formula (V) can be di-p-nitrophenyl adipate, di-p-nitrophenyl sebacinate, or di-p-nitrophenyl dodecyldicarboxylate; p/(p+m) can be about 0.9 to about 0.1; and m/(p+m) can be about 0.1 to about 0.9. The contacting can be carried out in the presence of a base, wherein the base can be triethylamine. The contacting can also be carried out in the presence of a solvent, wherein the solvent can be N,N-dimethylacetamide. The contacting can also be carried out at a temperature of about 50° C. to about 100° C. The contacting can preferably occur for about 10 hours to about 24 hours. The polymer of formula (VII) can also optionally be purified.

The present invention also provides a polymer of formula (XI):

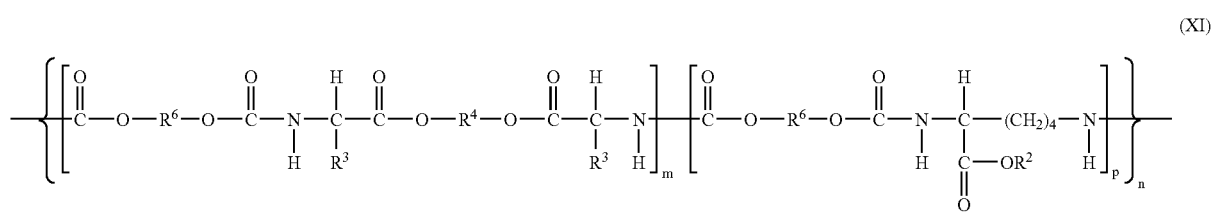

wherein
  m is about 0.1 to about 0.9;
  p is about 0.9 to about 0.1;
  n is about 50 to about 150;
  each $R^2$ is independently hydrogen, or $(C_6-C_{10})$aryl$(C_1-C_6)$alkyl;
  each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl;
  each $R^4$ is independently $(C_2-C_2)$alkylene; and
  each $R^6$ is independently $(C_2-C_{20})$alkylene or $(C_2-C_8)$alkyloxy$(C_2-C_{20})$alkylene;
comprising one or more subunits of the formula (VIII):

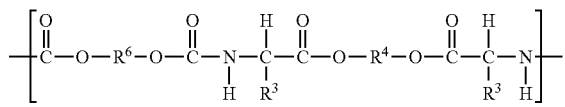

(VIII)

wherein
  each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and
  $R^4$ is independently $(C_2-C_{20})$alkylene;
  $R^6$ is independently $(C_2-C_{20})$alkylene or $(C_2-C_8)$alkyloxy$(C_2-C_{20})$alkylene;
and
one or more subunits of the formula (IX):

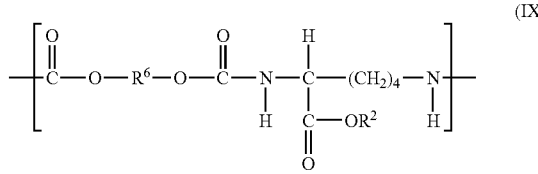

(IX)

wherein
  the total number of subunits (VIII) and (IV) is about 50 to about 150;
  $R^2$ is independently hydrogen, $(C_1-C_6)$alkyl, or $(C_6-C_{10})$aryl$(C_1-C_6)$alkyl.
  Specifically, $R^2$ can independently be hydrogen or benzyl; each $R^3$ can independently be iso-butyl or benzyl; $R^4$ can independently be $(CH_2)_4$, $(CH_2)_6$, $(CH_2)_8$, or $(CH_2)_{12}$; and $R^6$ can independently be $(CH_2)_3$ or $(CH_2)_2$—O—$(CH_2)_2$.
  The present invention also provides a polymer of formula (XI):

wherein
  m is about 0.1 to about 0.9;
  p is about 0.9 to about 0.1;
  n is about 50 to about 150;
  each $R^2$ is independently hydrogen, or $(C_6-C_{10})$aryl$(C_1-C_6)$alkyl;
  each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl;
  each $R^4$ is independently $(C_2-C_{20})$alkylene; and
  each $R^6$ is independently $(C_2-C_{20})$alkylene or $(C_2-C_8)$alkyloxy$(C_2-C_{20})$alkylene.
  Specifically, each $R^2$ can independently be hydrogen or benzyl; each $R^3$ can independently be iso-butyl or benzyl; each $R^4$ can independently be $(CH_2)_4$, $(CH_2)_6$, $(CH_2)_8$, or $(CH_2)_{12}$; each $R^6$ can independently be $(CH_2)_3$ or $(CH_2)_2$—O—$(CH_2)_2$; p/(p+m) can be about 0.9 to about 0.1; and m/(p+m) can be about 0.1 to about 0.9.
  The present invention also provides a polymer of formula (XI) formed from an amount of one or more compounds of formula (III):

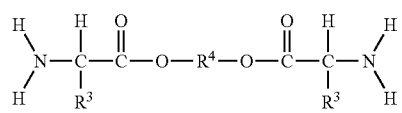

(III)

wherein
  each $R^3$ is independently hydrogen, $(C_1-C_6)$alkyl, $(C_2-C_6)$alkenyl, $(C_2-C_6)$alkynyl, or $(C_6-C_{10})$aryl$(C_1C_6)$alkyl; and
  $R^4$ is independently $(C_2-C_{20})$alkylene; or a suitable salt thereof; and an amount of one or more compounds of formula (IV):

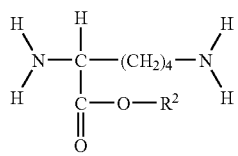

(IV)

wherein
  $R^2$ is independently hydrogen, or $(C_6-C_{10})$aryl$(C_1-C_6)$alkyl; or a suitable salt thereof; and

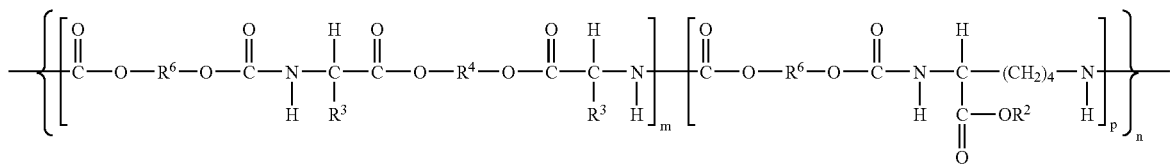

(XI)

an amount of one or more compounds of formula (X):

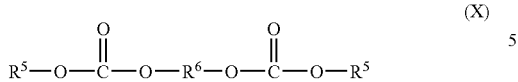

wherein
each $R^5$ is independently $(C_6-C_{10})$aryl optionally substituted with one or more nitro, cyano, halo, trifluoromethyl, or trifluoromethoxy; and
$R^6$ is independently $(C_2-C_{20})$alkylene or $(C_2-C_8)$alkyloxy $(C_2-C_{20})$alkylene.

Specifically, $R^2$ can independently be hydrogen or benzyl; each $R^3$ can independently be iso-butyl or benzyl; $R^4$ can independently be $(CH_2)_4$, $(CH_2)_6$, $(CH_2)_8$, or $(CH_2)_{12}$; each $R^5$ can be p-nitrophenyl; $R^6$ can independently be $(CH_2)_3$ or $(CH_2)_2$—O—$(CH_2)_2$; the compound of formula (III) can be the di-p-tolunesulfonic acid salt of a bis-(L-α-amino acid) α,ω-alkylene diester; the compound of formula (IV) can be the di-p-tolunesulfonic acid salt of L-lysine benzyl ester, the compound of formula (X) can be 1,3-bis (4-nitro-phenoxycarbonyloxy) propane; or 2,2'-bis-4-nitrophenoxycarbonyloxy ethylether, p/(p+m) can be about 0.9 to about 0.1; and m/(p+m) can be about 0.1 to about 0.9.

The present invention also provides a method for preparing a polymer of formula (XI):

or a suitable salt thereof; and
an amount of one or more compounds of formula (V):

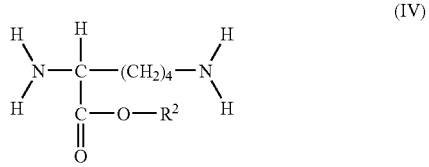

or a suitable salt thereof; and
an amount of one or more compounds of formula (X):

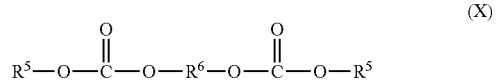

under suitable conditions to provide the polymer of formula (XI).

Specifically, each $R^2$ can independently be hydrogen or benzyl; each $R^3$ can independently be iso-butyl or benzyl; each $R^4$ can independently be $(CH_2)_4$, $(CH_2)_6$, $(CH_2)_8$, or $(CH_2)_{12}$; each $R^5$ can be p-nitrophenyl; each $R^6$ can inde-

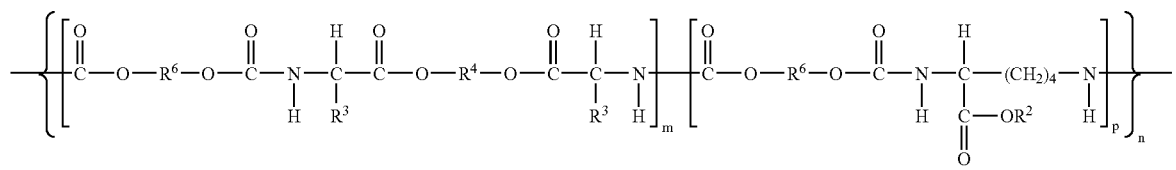

wherein
m is about 0.1 to about 0.9;
p is about 0.9 to about 0.1;
n is about 50 to about 150;
each $R^2$ is independently hydrogen or $(C_6-C_{10})$aryl$(C_1-C_6)$alkyl;
each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl;
each $R^4$ is independently $(C_2-C_{20})$alkylene;
each $R^5$ is independently $(C_6-C_{10})$aryl optionally substituted with one or more nitro, cyano, halo, trifluoromethyl, or trifluoromethoxy; and
each $R^6$ is independently $(C_2-C_{20})$alkylene or $(C_2-C_8)$alkyloxy$(C_2-C_{20})$alkylene;
comprising contacting an amount of one or more compounds of formula (III):

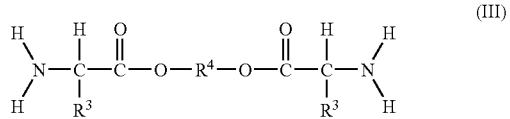

pendently be $(CH_2)_3$ or $(CH_2)_2$—O—$(CH_2)_2$; the compound of formula (III) can be the di-p-tolunesulfonic acid salt of a bis-(L-α-amino acid)-α,ω-alkylene diester; the compound of formula (IV) can be the di-p-tolunesulfonic acid salt of L-lysine benzyl ester, the compound of formula (X) can be 1,3-bis (4-nitro-phenoxycarbonyloxy) propane, or 2,2'-bis-4-nitrophenoxycarbonyloxy ethylether; p/(p+m) can be about 0.9 to about 0.1; and m/(p+m) can be about 0.1 to about 0.9. The contacting can be carried out in the presence of a base, wherein the base can be triethylamine. The contacting can be carried out in the presence of a solvent, wherein the solvent can be N,N-dimethylacetamide. The contacting can be carried out at a temperature of about 50° C. to about 100° C. The contacting can occur for about 10 hours to about 24 hours. In addition, the polymer of formula (XI) can optionally be purified.

The biodegradation of the copolyester amides and copolyester urethanes of the present invention allows the delivery of essential α-amino acids to targeted sites (e.g., to facilitate wound repair of injured tissues). In addition, the polymers of the present invention can be used for the attachment free iminoxyl radicals for suppressing inconsolable cell proliferation, and heparin or hirudin for increasing hemocompatibility. These modified polymers can be used to coat stents to suppress restenosis. In addition, the polymers of the present invention can be used as polyacids for the application in gynecology as impregnated contraceptive agents, e.g., for the controlled release of ferrous gluconate and the like. Furthermore, the polymers of the present invention can be used as polyacids for the attachment of unsaturated compounds, e.g., allyl amine or allyl alcohol, to obtain photo-curable and cross-linkable biodegradable polymers. The present polymers can be cross-linked with other polymers containing double bonds to create hybrid materials.

The biological and material properties of the polymers of the present invention can be varied over a wide range because the polymers can be formed from starting materials having varying functional groups (e.g., dicarboxylic acids, diols, and α-amino acids). See, e.g., Examples 1-22. In contrast to conventional poly(α-amino acids), the elastomeric functional copolyester amides and copolyester urethanes of the present invention can be obtained in high yields. See, Table III. For example, the compounds of the present invention can be prepared in yields up to about 97%. In addition, the reaction conditions employed to prepare the polymers of the present invention are relatively simple and the reagents are relatively inexpensive.

The present invention also provides a polymer of formula (VII) that is linked to one or more drugs. The present invention also provides a polymer of formula (XI) that is linked to one or more drugs. A residue of the polymer can be linked directly to a residue of the drug. The residue of the polymer can be linked directly to the residue of the drug through an amide, ester, ether, amino, ketone, thioether, sulfinyl, sulfonyl, disulfide, or a direct linkage. The residue of the polymer can be linked directly to the residue of the drug through one of the following linkages: —N(R)C(=O)—, —C(=O)N(R)—, —OC(=O)—, —C(=O)O—, —O—, —C(=O)—, —S—, —S(O)—, —S(O)$_2$—, —S—S—, —N(R)—, or C—C; wherein each R is independently H or (C$_1$-C$_6$)alkyl.

A residue of the polymer can be linked to a residue of the drug, through a linker. The linker can separate the residue of the polymer and the residue of the drug by about 5 angstroms to about 200 angstroms, inclusive, in length. The residue of the polymer can be linked to the linker and the linker can be linked to the residue of the drug, independently, through an amide, ester, ether, amino, ketone, thioether, sulfinyl, sulfonyl, disulfide, or a direct linkage. The residue of the polymer can be linked to the linker and the linker can be linked to the residue of the drug, independently, through one of the following linkages: —N(R)C(=O)—, —C(=O)N(R)—, —OC(=O)—, —C(=O)O—, —O—, —C(=O)—, —S—, —S(O)—, —S(O)$_2$—, —S—S—, —N(R)—, or C—C; wherein each R is independently H or (C$_1$-C$_6$)alkyl. The linker can be a divalent radical of the formula W-A-Q wherein A is (C$_1$-C$_{24}$)alkyl, (C$_2$-C$_{24}$)alkenyl, (C$_2$-C$_{24}$)alkynyl, (C$_3$-C$_8$)cycloalkyl, or (C$_6$-C$_{10}$)aryl, wherein W and Q are each independently —N(R)C(=O)—, —C(=O)N(R)—, —OC(=O)—, —C(=O)O—, —O—, —S—, —S(O)—, —S(O)$_2$—, —S—S—, —N(R)—, —C(=O)—, or a direct bond; wherein each R is independently H or (C$_1$-C$_6$)alkyl. The linker can be a 1,ω-divalent radical formed from a peptide or an amino acid. The peptide can comprise 2 to about 25 amino acids. The peptide can be poly-L-lysine, poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-arginine, or poly-L-lysine-L-tyrosine.

The one or more drugs can each independently be: a polynucleotide, polypeptide, oligonucleotide, gene therapy agent, nucleotide analog, nucleoside analog, polynucleic acid decoy, therapeutic antibody, abciximab, anti-inflammatory agent, blood modifier, anti-platelet agent, anti-coagulation agent, immune suppressive agent, anti-neoplastic agent, anti-cancer agent, anti-cell proliferation agent, or nitric oxide releasing agent.

The present invention also provides a formulation comprising a polymer of formula (VII) and one or more drugs. The present invention also provides a formulation comprising a polymer of formula (XI) and one or more drugs. The one or more drugs can each independently be: a polynucleotide, polypeptide, oligonucleotide, gene therapy agent, nucleotide analog, nucleoside analog, polynucleic acid decoy, therapeutic antibody, abciximab, anti-inflammatory agent, blood modifier, anti-platelet agent, anti-coagulation agent, immune suppressive agent, anti-neoplastic agent, anti-cancer agent, anti-cell proliferation agent, or nitric oxide releasing agent.

The present invention also provides a method of using a polymer of the present invention for use as a medical device, a pharmaceutical, a carrier for covalent immobilization of a drug, or a bioactive substance.

DETAILED DESCRIPTION OF THE INVENTION

Figure 1:
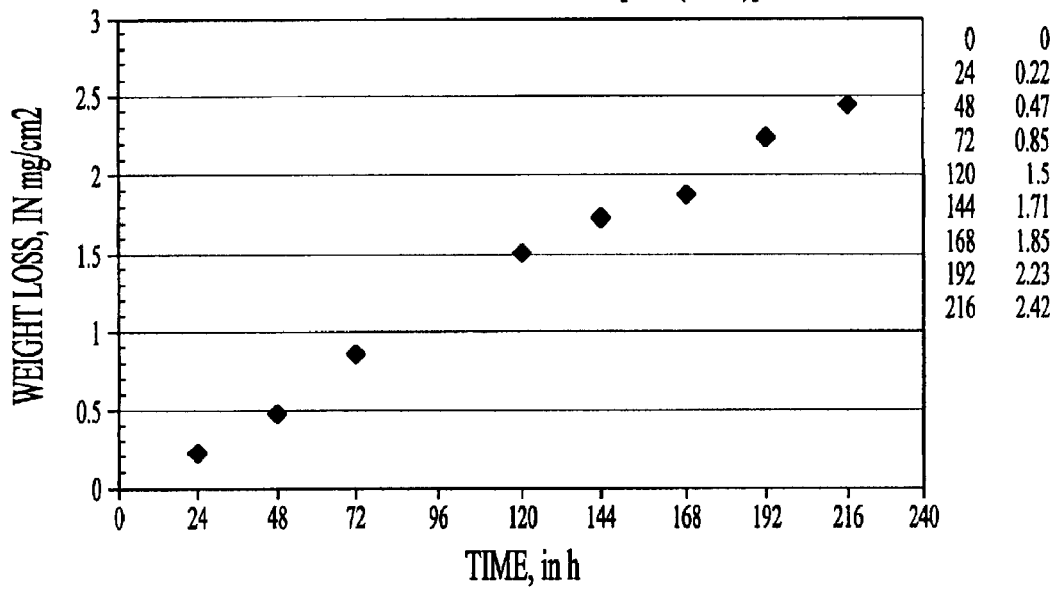
FIG. 1 illustrates the biodegradation (weight loss in mg/cm$^2$) of 4-amino TEMPO ("TAM") attached to a representative compound, co-PEA, according to one embodiment.

The following definitions are used, unless otherwise described: halo can be chloro, fluoro, bromo, or iodo. Alkyl, alkenyl, alkynyl, etc. denote both straight and branched groups; but reference to an individual radical such as "propyl" embraces only the straight chain radical, a branched chain isomer such as "isopropyl" being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, -butyl, iso-butyl, n-hexyl, n-decyl, tetradecyl, and the like. As used herein, "alkyl" includes "substituted alkyl," which refers to an alkyl group as defined above, having from 1 to 8 substituents, preferably 1 to 5 substituents, and more preferably 1 to 3 substituents, selected from the group consisting of alkoxy, cycloalkyl, acyl, amino, azido, cyano, halogen, hydroxyl, keto, thioketo, carboxy, thiol, aryl, heteroaryl, heterocyclic, and nitro.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups allyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. As used herein, "alkoxy" includes "substituted alkoxy," which refers to the groups substituted alkyl-O—, substituted alkenyl-O—, substituted cycloatkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1-6 sites of vinyl unsaturation. Preferred alkenyl groups include ethenyl (—CH=CH$_2$), in-propenyl (—CH$_2$CH=CH$_2$), iso-propenyl (—C(CH$_3$)=CH$_2$), and the like. As used herein, "alkenyl" includes "substituted alkenyl," which refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1-6 sites of acetylene (triple bond) unsaturation. Preferred alkynyl groups include ethynyl (—C≡CH), propargyl (—CH$_2$C≡CH) and the like. As used herein, "alkynyl" includes "substituted alkynyl," which refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of hydroxy, thiol, acyl, alkyl alkoxy, alkenyl, alkynyl, cycloalkyl aryl, azido, carboxy, cyano, halo, nitro, heteroaryl, heterocyclic, sulfonamide. Preferred aryl substituents include alkyl, alkoxy, halo, cyano, nitro, and trihalomethyl.

The term "amino" refers to the group —NH$_2$.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. As used herein, "cycloalkyl" includes "substituted cycloalkyl," which refers to cycloalkyl groups having from 1 to 5 substituents, and preferably 1 to 3 substituents, selected from the group consisting of alkoxy, cycloalkyl, acyl, amino, azido, cyano, halogen, hydroxyl, keto, carboxy, thiol, aryl, heteroaryl, heterocyclic, and nitro.

The term "halo" or "halogen" refers to fluoro, chloro, bromo and iodo.

"Haloalkyl" refers to allyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of hydroxy, thiol, acyl, alkyl, alkoxy, alkenyl, alkynyl, cycloalkyl, alkaryl, aryl, azido, carboxy, cyano, halo, nitro, heteroaryl, and heterocyclic. Preferred aryl substituents include alkyl, alkoxy, halo, cyano, nitro, and trihalomethyl. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, cycloalkyl, acyl, amino, azido, cyano, halogen, hydroxyl, keto, carboxy, thiol, aryl, and heterocyclic. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "saccharide group" refers to an oxidized, reduced or substituted saccharide monoradical covalently attached to the glycopeptide or other compound via any atom of the saccharide moiety, preferably via the aglycone carbon atom. The term includes amino-containing saccharide groups. Representative saccharides include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. For the purposes of this definition, these saccharides are referenced using conventional three letter nomenclature and the saccharides can be either in their open or preferably in their pyranose form. The "saccharide group" includes "amino-containing saccharide group" or "amino saccharide," which refers to a saccharide group having an amino substituent. Representative amino-containing saccharides include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

The term "stereoisomer" as it relates to a given compound is well understood in the art, and refers another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, *Morrison and Boyde Organic Chemistry*, 1983, 4th ed., Allyn and Bacon, Inc., Boston, Mass., page 123.

The term "thiol" refers to the group —SH.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Cyclodextrin" refers to cyclic molecules containing six or more α-D-glucopyranose units linked at the 1,4 positions by a linkages as in amylose. β-Cyclodextrin or cycloheptaamylose contains seven α-D-glucopyranose units. As used herein, the term "cyclodextin" also includes cyclodextrin derivatives such as hydroxypropyl and sulfobutyl ether cyclodextrins, and others. Such derivatives are described for example, in U.S. Pat. Nos. 4,727,064 and 5,376,645. Additionally, hydroxypropyl-β-cyclodextrin and sulfobutyl-β-cyclodextrin are commercially available. One preferred cyclodextrin is hydroxypropyl β-cyclodextrin having a degree of substitution of from about 4.1-5.1 as measured by FUR. Such a cyclodextrin is available from Cerestar (Hammond, Ind., USA) under the name Cavitron™ 82003.

As used herein, an "amino acid" is a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a $(C_1-C_6)$alkyl, phenyl or benzyl ester or amide). Other suitable amino and carboxy protecting groups are known to those skilled in the art (See for example, T. W. Greene, *Protecting Groups In Organic Synthesis*; Wiley: New York, 1981; D. Voet, *Biochemistry*, Wiley: New York, 1990; L. Stryer, *Biochemistry*, (3rd Ed.), W. H. Freeman and Co.: New York, 1975; J. March, *Advanced Organic Chemistry. Reactions, Mechanisms and Structure*, (2nd Ed.), McGraw Hill: New York, 1977; F. Carey and R. Sundberg, *Advanced Organic Chemistry. Part B: Reactions and Synthesis*, (2nd Ed.), Plenum: New York, 1977; and references cited therein). According to the invention, the amino or carboxy protecting group can also comprise a non-metallic radionuclide (e.g., Fluorine-18, Iodine-123, or Iodine-124).

The term "amino acid" includes alpha amino acids and beta amino acids. The alpha amino acids include monocarboxylic monoamino acids, dicarboxylic monoamino acids, polyamino acids and heterocyclic amino acids. Examples of monocarboxylic monoamino acids include glycine, alpha-phenylglycine, alpha-alanine, serine, valine, norvaline, beta-mercaptovaline, threonine, cysteine, leucine, isoleucine, norleucine, N-methylleucine, beta-hydroxy leucine, methionine, phenylalanine, N-methylphenylalanine, pipecolic acid, sarcosine, selenocysteine, tyrosine, 3,5-diiodotyrosine, triiodothyronine, and thyroxine. Examples of monoamino dicarboxylic acids and amides include aspartic acid, beta-methyl aspartic acid, glutamic acid, asparagine, alpha-aminoadipic acid, 4-keto-pipecolic acid, lanthionine, and glutamine. Examples of polyamino acids include ornithine, lysine, 6-N-methyllysine, 5-hydroxylysine, desmosine, arginine and cystine. Examples of heterocyclic amino acids include proline, 4-hydroxyproline and histidine, and tryptophan. Examples of other alpha amino acids are gamma-carboxyglutamate and citrulline. The beta amino acids include, for example, beta-alanine.

As used herein, a "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

Specific and preferred values listed below for radicals, substituents, and ranges, are for illustration only; they do not exclude other defined values or other values within defined ranges for the radicals and substituents.

A specific value for $R^1$ is $(CH_2)_4$, $(CH_2)_8$, or $(CH_2)_{12}$.

A specific value for $R^2$ is hydrogen, benzyl, or phenethyl. Another specific value for $R^2$ is benzyl.

A specific value for $R^3$ is iso-butyl or benzyl.

A specific value for $R^4$ is $(CH_2)_4$, $(CH_2)_6$, $(CH_2)_8$, or $(CH_2)_{12}$.

A specific value for $R^5$ is p-nitrophenyl.

A specific value for $R^6$ is $(CH_2)_3$ or $(CH_2)_2$—O—$(CH_2)_2$.

A specific value for m is about 0.25 to about 0.75.

A specific value for p is about 0.75 to about 0.25.

A specific value for n is about 75 to about 125.

A specific value for p/(p+m) is about 0.75 to about 0.25.

A specific value for m/(p+m) is about 0.25 to about 0.75.

A specific value for (p+m) is about 0.9 to about 1.1. Another specific value for (p+m) is about 0.75 to about 1.25.

A specific group of compounds of formula (III) are the di-p-tolunesulfonic acid salts of a bis-(L-α-amino acid)α,ω-alkylene diester:

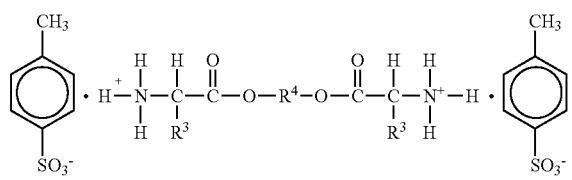

wherein
each $R^3$ is independently iso-butyl or benzyl; and
$R^4$ is $(CH_2)_4$, $(CH_2)_6$, $(CH_2)_8$, or $(CH_2)_{12}$.

A specific group of compounds of formula (IV) are the di-p-tolunesulfonic acid salts of L-lysine arylalkyl esters:

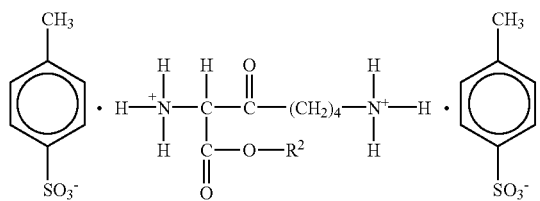

wherein
$R^2$ is benzyl or phenethyl. More specifically, $R^2$ can be benzyl.

A specific group of compounds of formula (V) are compounds of the formula:

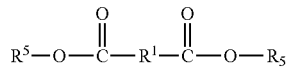

wherein
$R^1$ is $(CH_2)_4$ $(CH_2)_8$, or $(CH_2)_{12}$; and
$R^5$ is p-nitrophenyl.

For example, a specific group of compounds of formula (V) are di-p-nitrophenyl adipate, di-p-nitrophenyl sebacinate, and di-p-nitrophenyl dodecyldicarboxylate A specific group of compounds of formula (X) are compounds of the formula:

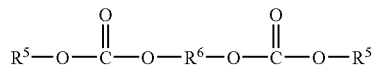

wherein
$R^5$ is p-nitrophenyl; and
$R^6$ is $(CH_2)_3$ or $(CH_2)_2$—O—$(CH_2)_2$.

For example, a specific group of compounds of formula (X) are 1,3-bis (4-nitro-phenoxycarbonyloxy) propane and 2,2'-bis-4-(nitrophenoxycarbonyloxy)ethylether.

In cases where compounds (e.g., starting materials) are sufficiently basic or acidic to form stable nontoxic acid or base salts, the compounds can exist as the acceptable salt. Examples of acceptable salts are organic acid addition salts formed with acids which form an acceptable anion, for example, tosylate, methanesulfonate, acetate, citrate, malonate, tararate, succinate, benzoate, ascorbate, α-ketoglutarate, and α-glycerophosphate. Suitable inorganic salts may also exist, including hydrochloride, sulfate, nitrate, bicarbonate, and carbonate salts.

Acceptable salts may be obtained by using standard procedures that are well known in the art, for example by reacting a sufficiently basic compound such as an amine with a suitable acid affording an acceptable anion. Alkali metal (for example, sodium, potassium or lithium) or alkaline earth metal (for example calcium) salts of carboxylic acids can also be made.

Processes for preparing polymers of the present invention (e.g., polymers of formula (VII) and polymers of formula (XI)) are provided as further embodiments of the invention and are illustrated by the procedures herein below in which the meanings of the generic radicals are as given above unless otherwise qualified.

A polymer of formula (VII) can include one or more subunits of formula (I) and one or more subunits of formula (II); As such, a polymer of formula (VII) can be prepared from a compound of formula (III), from a compound of formula (IV), and from a compound of formula (V). Specifically, a polymer of formula (VII) can be prepared by contacting a compound of formula (III), a compound of formula (IV), and a compound of formula (V) under suitable conditions to provide a polymer of formula (VII).

The compounds of formula (III), (IV), and (V) can be contacted in the presence of a solvent. Any suitable solvent can be employed. When the compounds of formula (III), (IV), and (V) are contacted in the presence of a solvent, the compounds of formula (III), (IV), and (V) are preferably soluble in the solvent. One exemplary suitable solvent is N,N-dimethylacetamide.

The compounds of formula (III), (IV), and (V) can be contacted in the presence of a base. Any suitable base can be employed. When the compounds of formula (III), (IV), and (V) are contacted in the presence of a base, the base will preferably adjust the initial pH of the reaction mixture (i.e., the solution including the compounds of formula (III), (IV), and (V)) above about 7. The base is useful to yield the free amines of the compound of formula (III) and the compound of formula (IV). One exemplary suitable base is triethylamine.

The compounds of formula (III), (IV), and (V) can be contacted for a period of time sufficient to provide the polymer of formula (VII). For example, the period of time can be from about 1 hour to about 48 hours, inclusive. Preferably, the period of time can be from about 5 hours to about 30 hours, inclusive. More preferably, the period of time can be from about 10 hours to about 24 hours, inclusive.

The compounds of formula (III), (IV), and (V) can be contacted at a temperature sufficient to provide the polymer of formula (VII). For example, the temperature can be from the freezing point of the liquid reaction mixture (e.g., the solvent, base, and the compounds of formula (III), (IV), and (V)) up to about the reflux temperature of the reaction mixture. Preferably, the temperature can be from about 25° C. to about 150° C. More preferably, the temperature can be from about 50° C. to about 100° C.

A polymer of formula (XI) can include one or more subunits of formula (VIII) and one or more subunits of formula (IX). As such, a polymer of formula (XI) can be prepared from a compound of formula (III), from a compound of formula (IV), and from a compound of formula (X). Specifically, a polymer of formula (XI) can be prepared by contacting a compound of formula (III), a compound of formula (IV), and a compound of formula (X) under suitable conditions to provide a polymer of formula (XI).

The compounds of formula (III), (IV), and (X) can be contacted in the presence of a solvent. Any suitable solvent can be employed. When the compounds of formula (III), (IV), and (X) are contacted in the presence of a solvent, the compounds of formula (III), (IV), and (X) are preferably soluble in the solvent. One exemplary suitable solvent is N,N-dimethylacetamide.

The compounds of formula (III), (IV), and (X) can be contacted in the presence of a base. Any suitable base can be employed. When the compounds of formula (III), (IV), and (X) are contacted in the presence of a base, the base will preferably adjust the initial pH of the reaction mixture (i.e., the solution including the compounds of formula (III), (IV), and (X)) above about 7. The base is useful to yield the free amines of the compound of formula (III) and the compound of formula (IV). One exemplary suitable base is triethylamine.

The compounds of formula (III) (IV), and (X) can be contacted for a period of time sufficient to provide the polymer of formula (VII). For example, the period of time can be from about 1 hour to about 48 hours, inclusive. Preferably, the period of time can be from about 5 hours to about 30 hours, inclusive. More preferably, the period of time can be from about 10 hours to about 24 hours, inclusive.

The compounds of formula (III), (IV), and (X) can be contacted at a temperature sufficient to provide the polymer of formula (VII). For example, the temperature can be from about the freezing point of the liquid reaction mixture (e.g., the solvent, base, and the compounds of formula (III) (IV), and (X)) up to about the reflux temperature of the reaction mixture. Preferably, the temperature can be from about 25° C. to about 150° C. More preferably, the temperature can be from about 50° C. to about Polymer and Drug A polymer of the present invention can include one or more drugs. In one embodiment, a polymer of the present invention can be physically intermixed with one or more drugs. In another embodiment, a polymer of the present invention can be linked to one or more drugs, either directly or through a linker. In another embodiment, a polymer of the present invention can be linked to one or more drugs, either directly or through a linker, and the resulting polymer can be physically intermixed with one or more drugs.

As used herein, a "polymer of the present invention" includes a compound of formula (VII), a compound of formula (XI), or a combination thereof.

Polymer/Drug Linkage

The present invention provides a polymer of the present invention (e.g., a compound of formula (VII) or a compound of formula (XI)) directly linked to one or more drugs. In such an embodiment, the residues of the polymer can be linked to the residues of the one or more drugs. For example, one residue of the polymer can be directly linked to one residue of the drug. The polymer and the drug can each have one open valence. Alternatively, more than one drug can be directly linked to the polymer. In such an embodiment, the residue of each drug can be linked to a corresponding residue of the polymer. As such, the number of residues of the one or more drugs can correspond to the number of open valences on the residue of the polymer.

As used herein, a "residue of a polymer of the present invention" refers to a radical of a polymer of the present invention having one or more open valences. Any synthetically feasible atom, atoms, or functional group of the polymer (e.g., on the polymer backbone or pendant group) of the present invention can be removed to provide the open valence, provided bioactivity is substantially retained when the radical is attached to a residue of a drug. Additionally, any synthetically feasible functional group (e.g., carboxyl) can be created on the polymer (e.g., on the polymer backbone or pendant group) to provide the open valence, provided bioactivity is substantially retained when the radical is attached to a residue of a drug. Based on the linkage that is desired, one skilled in the art can select suitably functionalized starting materials that can be derived from the polymer of the present invention using procedures that are known in the art.

As used herein, a "residue of a compound of formula (VII)" refers to a radical of a compound of formula (VII) having one or more open valences. Any synthetically feasible atom, atoms, or functional group of the compound of formula (VII) (e.g., on the polymer backbone or pendant group) can be removed to provide the open valence, provided bioactivity is substantially retained when the radical is attached to a residue of a drug. Additionally, any synthetically feasible functional group (e.g., carboxyl) can be created on the compound of formula (VII) (e.g., on the polymer backbone or pendant group) to provide the open valence, provided bioactivity is substantially retained when the radical is attached to a residue of a drug. Based on the linkage that is desired, one skilled in the art can select suitably functionalized staring materials that can be derived from the compound of formula (VII) using procedures that are known in the art.

As used herein, a "residue of a compound of formula (XI)" refers to a radical of a compound of formula (XI)

having one or more open valences. Any synthetically feasible atom, atoms, or functional group of the compound of formula (XI) (e.g., on the polymer backbone or pendant group) can be removed to provide the open valence, provided bioactivity is substantially retained when the radical is attached to a residue of a drug. Additionally, any synthetically feasible functional group (e.g., carboxyl) can be created on the compound of formula (XI) (e.g., on the polymer backbone or pendant group) to provide the open valence, provided bioactivity is substantially retained when the radical is attached to a residue of a drug. Based on the linkage that is desired, one skilled in the art can select suitably functionalized starting materials that can be derived from the compound of formula (XI) using procedures that are known in the art.

The residue of a drug can be linked to the residue of a compound of formula (VII) or (XI) through an amide (e.g., —N(R)C(=O)— or —C(=O)N(R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), disulfide (e.g., —S—S—), or a direct (e.g., C—C bond) linkage, wherein each R is independently H or ($C_1$-$C_6$)alkyl. Such a linkage can be formed from suitably functionalized starting materials using synthetic procedures that are known in the art. Based on the linkage that is desired, one skilled in the art can select suitably functional starting materials that can be derived from a residue of a compound of formula (VII) or (XI) and from a given residue of a drug using procedures that are known in the art. The residue of the drug can be directly linked to any synthetically feasible position on the residue of a compound of formula (VII) or (XI). Additionally, the invention also provides compounds having more than one residue of a drug or drugs directly linked to a compound of formula (VII) or (XI).

One or more drugs can be linked directly to the polymer. Specifically, the residue of each of the drugs can each be directly linked to the residue of the polymer. Any suitable number of drugs (i.e., residues thereof) can be directly linked to the polymer (i.e., residue thereof). The number of drugs that can be directly linked to the polymer can typically depend upon the molecular weight of the polymer. For example, for a compound of formula (VII), wherein n is about 50 to about 150, up to about 450 drugs (i.e., residues thereof) can be directly linked to the polymer (i.e., residue thereof), up to about 300 drugs (i.e., residues thereof) can be directly linked to the polymer (i.e., residue thereof), or up to about 150 drugs (i.e., residues thereof) can be directly linked to the polymer (i.e., residue thereof). Likewise, for a compound of formula (XI), wherein n is about 50 to about 150, up to about 450 drugs (i.e., residues thereof) can be directly linked to the polymer (i.e., residue thereof), up to about 300 drugs (i.e., residues thereof) can be directly linked to the polymer (i.e., residue thereof), or up to about 150 drugs (i.e., residues thereof) can be directly linked to the polymer (i.e., residue thereof).

The residue of a polymer of the present invention, the residue of a compound of formula (VII), and/or the residue of a compound of formula (XI) can be formed employing any suitable reagents and reaction conditions. Suitable reagents and reaction conditions are disclosed, e.g., in *Advanced Organic Chemistry Part B: Reactions and Synthesis*, Second Edition, Carey and Sundberg (1983); *Advanced Organic Chemistry, Reactions, Mechanisms, and Structure*, Second Edition, March (1977); and *Comprehensive Organic Transformations*, Second Edition, Larock (1999).

In one embodiment of the present invention, a polymer (i.e., residue thereof) of the present invention can be linked to the drug (i.e., residue thereof) via the carboxyl group (e.g., COOR$^2$) of the polymer. Specifically, a compound of formula (VII), wherein R$^2$ is independently hydrogen, or ($C_6$-$C_{10}$)aryl($C_1$-$C_6$)alkyl; a compound of formula (XI), wherein R$^2$ is independently hydrogen, or ($C_6$-$C_{10}$)aryl($C_1$-$C_6$)alkyl; or a combination thereof, can react with an amino functional group of the drug or a hydroxyl functional group of the drug, to provide a Polymer/Drug having an amide linkage or a Polymer/Drug having a carboxylic ester linkage, respectively. In another embodiment, the carboxyl group of the polymer can be transformed into an acyl halide or an acyl anhydride.

Drug

As used herein, a "drug" refers to a therapeutic agent or a diagnostic agent and includes any substance, other than food, used in the prevention, diagnosis, alleviation, treatment, or cure of a disease. *Stedman's Medical Dictionary*, 25$^{th}$ Edition, Illustrated (1990) p. 486. The substance can be taken by mouth; injected into a muscle, the skin, a blood vessel, or a cavity of the body; or topically applied. *Mosby's Medical, Nursing & Allied Health Dictionary*, Fifth Edition, (1998) p. 516. The drug can include any substance disclosed in at least one of: *The Merck Index*, 12$^{th}$ Edition (1996); *Concise Dictionary of Biomedicine and Molecular Biology*, Pei-Show Juo, (1996); *U.S. Pharmacopeia Dictionary*, 2000 Edition; and *Physician's Desk Reference*, 2001 Edition.

Specifically, the drug can include, but is not limited to, one or more: polynucleotides, polypeptides, oligonucleotides, gene therapy agents, nucleotide analogs, nucleoside analogs, polynucleic acid decoys, therapeutic antibodies, abciximab, anti-inflammatory agents, blood modifiers, anti-platelet agents, anti-coagulation agents, immune suppressive agents, anti-neoplastic agents, anti-cancer agents, anti-cell proliferation agents, and nitric oxide releasing agents.

The polynucleotide can include deoxyribonucleic acid (DNA), ribonucleic acid (RNA), double stranded DNA, double stranded RNA, duplex DNA/RNA, antisense polynucleotides, functional RNA or a combination thereof. In one embodiment, the polynucleotide can be RNA. In another embodiment, the polynucleotide can be DNA In another embodiment, the polynucleotide can be an antisense polynucleotide. In another embodiment, the polynucleotide can be a sense polynucleotide. In another embodiment, the polynucleotide can include at least one nucleotide analog. In another embodiment, the polynucleotide can include a phosphodiester linked 3'-5' and 5'-3' polynucleotide backbone. Alternatively, the polynucleotide can include non-phosphodiester linkages, such as phosphotioate type, phosphoramidate and peptide-nucleotide backbones. In another embodiment, moieties can be linked to the backbone sugars of the polynucleotide. Methods of creating such linkages are well known to those of skill in the art.

The polynucleotide can be a single-stranded polynucleotide or a double-stranded polynucleotide. The polynucleotide can have any suitable length. Specifically, the polynucleotide can be about 2 to about 5,000 nucleotides in length, inclusive; about 2 to about 1000 nucleotides in length, inclusive; about 2 to about 100 nucleotides in length, inclusive; or about 2 to about 10 nucleotides in length, inclusive.

An antisense polynucleotide is typically a polynucleotide that is complimentary to an mRNA, which encodes a target protein. For example, the mRNA can encode a cancer promoting protein i.e., the product of an oncogene. The antisense polynucleotide is complimentary to the single stranded mRNA and will form a duplex and thereby inhibit expression of the target gene, i.e., will inhibit expression of the oncogene. The antisense polynucleotides of the invention can form a duplex with the mRNA encoding a target protein and will disallow expression of the target protein.

A "functional RNA" refers to a ribozyme or other RNA that is not translated.

A "polynucleic acid decoy" is a polynucleic acid which inhibits the activity of a cellular factor upon binding of the cellular factor to the polynucleic acid decoy. The polynucleic acid decoy contains the binding site for the cellular factor. Examples of cellular factors include, but are not limited to, transcription factors, polymerases and ribosomes. An example of a polynucleic acid decoy for use as a transcription factor decoy will be a double stranded polynucleic acid containing the binding site for the transcription factor. Alternatively, the polynucleic acid decoy for a transcription factor can be a single stranded nucleic acid that hybridizes to itself to form a snap-back duplex containing the binding site for the target transcription factor. An example of a transcription factor decoy is the E2F decoy. E2F plays role in transcription of genes that are involved with cell-cycle regulation and that cause cells to proliferate. Controlling E2F allows regulation of cellular proliferation. For example, after injury (e.g., angioplasty, surgery, stenting) smooth muscle cells proliferate in response to the injury. Proliferation may cause restenosis of the treated area (closure of an artery through cellular proliferation). Therefore, modulation of E2F activity allows control of cell proliferation and can be used to decrease proliferation and avoid closure of an artery. Examples of other such polynucleic acid decoys and target proteins include, but are not limited to, promoter sequences for inhibiting polymerases and ribosome binding sequences for inhibiting ribosomes. It is understood that the invention includes polynucleic acid decoys constructed to inhibit any target cellular factor.

A "gene therapy agent" refers to an agent that causes expression of a gene product in a target cell through introduction of a gene into the target cell followed by expression. An example of such a gene therapy agent would be a genetic construct that causes expression of a protein, such as insulin, when introduced into a cell. Alternatively, a gene therapy agent can decrease expression of a gene in a target cell. An example of such a gene therapy agent would be the introduction of a polynucleic acid segment into a cell that would integrate into a target gene and disrupt expression of the gene. Examples of such agents include viruses and polynucleotides that are able to disrupt a gene through homologous recombination. Methods of introducing and disrupting genes with cells are well known to those of skill in the art.

An oligonucleotide of the invention can have any suitable length. Specifically, the oligonucleotide can be about 2 to about 100 nucleotides in length, inclusive; up to about 20 nucleotides in length, inclusive; or about 15 to about 30 nucleotides in length, inclusive. The oligonucleotide can be single-stranded or double-stranded. In one embodiment, the oligonucleotide can be single stranded. The oligonucleotide can be DNA or RNA. In one embodiment, the oligonucleotide can be DNA In one embodiment, the oligonucleotide can be synthesized according to commonly known chemical methods. In another embodiment, the oligonucleotide can be obtained from a commercial supplier. The oligonucleotide can include, but is not limited to, at least one nucleotide analog, such as bromo derivatives, azido derivatives, fluorescent derivatives or a combination thereof. Nucleotide analogs are well known to those of skill in the art. The oligonucleotide can include a chain terminator. The oligonucleotide can also be used, e.g., as a cross linking reagent or a fluorescent tag. Many common linkages can be employed to couple an oligonucleotide of the invention to another moiety, e.g., phosphate, hydroxyl, etc. Additionally, a moiety may be linked to the oligonucleotide through a nucleotide analog incorporated into the oligonucleotide. In another embodiment, the oligonucleotide can include a phosphodiester linked 3'-5' and 5'-3' oligonucleotide backbone. Alternatively, the oligonucleotide can include non-phosphodiester linkages, such as phosphotioate type, phosphoramidate and peptide-nucleotide backbones. In another embodiment, moieties can be linked to the backbone sugars of the oligonucleotide. Methods of creating such linkages are well known to those of skill in the art.

Nucleotide and nucleoside analogues are well known on the art. Examples of such nucleoside analogs include, but are not limited to, Cytovene® (Roche Laboratories), Epivir® (Glaxo Wellcome), Gemzar® (Lilly), Hivid® (Roche Laboratories), Rebetron®) (Schering), Videx® (Bristol-Myers Squibb), Zerit® (Bristol-Myers Squibb), and Zovirax® (Glaxo Wellcome). See, *Physician's Desk Reference,* 2001 Edition.

Polypeptides of the invention can have any suitable length. Specifically, the polypeptides can be about 2 to about 5,000 amino acids in length, inclusive; about 2 to about 2,000 amino acids in length, inclusive; about 2 to about 1,000 amino acids in length, inclusive; or about 2 to about 100 amino acids in length, inclusive.

The polypeptides of the invention can also include "Peptide mimetics". Peptide analogs are commonly used in the pharmaceutical industry as non-peptide drugs with properties analogous to those of the template peptide. These types of non-peptide compound are termed "peptide mimetics" or "peptidomimetics". Fauchere, J. (1986) *Adv. Drug Res.,* 15:29; Veber and Freidinger (1985) *TINS* p. 392; and Evans et al. (1987) *J. Med. Chem.,* 30: 1229; and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —CH$_2$NH—, —CH$_2$S—, CH$_2$—CH$_2$—, —CH=CH—(cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Veea Data (arch 1983), Vol. 1, Issue 3, "Peptide Backbone Modifications" (general review); Morley, J. S., *Trends. Pharm. Sci.,* (1980) pp. 463468 (general review); Hudson, D. et al., *Int. J. Pept. Prot. Res.,* (1979) 14:177-185 (—CH$_2$ NH—, CH$_2$CH$_2$—); Spatola, A. F. et al., *Life Sci.* (1986) 38:1243-1249 (—CH$_2$—S—); Harm, M. M., *J. Chem. Soc. Perkin Trans I* (1982) 307-314 (—CH=CH—, cis and trans); Almquist, R. G. et al., *J. Med. Chem.,* (1980) 23:1392-1398 (—COCH$_2$—); Jennings-White, C. et al., *Tetrahedron Lett.,* (1982) 23:2533 (—COCH$_2$—) Szelke, M. et al., *European Appln.,* EP 45665 (1982) CA: 97:39405 (1982) (—CH(OH)CH$_2$—); Holladay, M. W. et al., *Tetrahedron Lett.,* (1983) 24:4401-4404 (—C (OH)CH$_2$—); and Hruby, V. J., *Life Sci.,* (1982) 31:189-199 (—CH$_2$—S—). Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a polypeptide with a D-amino acid of the same type (e.g., D-lysine in place of L-lysine) may be used to generate more stable polypeptides and polypeptides resistant to endogenous proteases.

In one embodiment, the polypeptide can be an antibody. Examples of such antibodies include single-chain antibodies, chimeric antibodies, monoclonal antibodies, polyclonal antibodies, antibody fragments, Fab fragments, IgA, IgG, IgK, IgD, IgE and humanized antibodies. In one embodiment, the antibody can bind to a cell adhesion molecule, such as a cadherin, integrin or selectin. In another embodiment, the antibody can bind to an extracellular matrix molecule, such as collagen, elastin, fibronectin or laminin. In still another embodiment, the antibody can bind to a receptor, such as an adrenergic receptor, B-cell receptor, complement receptor, cholinergic receptor, estrogen receptor, insulin receptor, low-density lipoprotein receptor, growth factor receptor or T-cell receptor. Antibodies of the invention can also bind to platelet aggregation factors (e.g., fibrinogen), cell proliferation factors (e.g., growth factors and cytokines), and blood clotting factors (e.g., fibrinogen). In another embodiment, an antibody can be conjugated to an active agent, such as a toxin. In another embodiment, the antibody can be Abciximab (ReoProR)). Abciximab is an Fab fragment of a chimeric antibody that binds to beta(3) integrins. Abciximab is specific for platelet glycoprotein IIb/IIIa receptors, e.g., on blood cells. Human aortic smooth muscle cells express alpha(v)beta(3) integrins on their surface. Treating beta(3) expressing smooth muscle cells may prohibit adhesion of other cells and decrease cellular migration or proliferation, thus reducing restinosis following percutaneous coronary interventions (CPI) e.g., stenosis, angioplasty, stenting. Abciximab also inhibits aggregation of blood platelets.

In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in J. Amer. Chem. Soc., 1996, 118, 13107-13108; J. Amer. Chem. Soc., 1997, 119, 12041-12047; and J. Amer. Chem. Soc., 1994, 116, 4573-4590. Representative glycopeptides include those identified as A477, A35512, A40926, A41030, A42867, A47934, A80407, A82846, A83850 A84575, AB-65, Actaplanin, Actinoidin, Ardacin, Avoparcin, Azureomycin, Balhimycin, Chloroorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics which have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur and phosphorous. Lipidated glycopeptide antibiotics are well-known in the art. See, for example, in U.S. Pat. Nos. 5,840,684, 5,843,889, 5,916,873, 5,919,756, 5,952,310, 5,977,062, 5,977,063, EP 667, 353, WO 98/52589, WO 99/56760, WO 00/04044, WO 00/39156, the disclosures of which are incorporated herein by reference in their entirety.

Anti-inflammatory agents include, e.g., analgesics (e.g., NSAIDS and salicylates), antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, Physician's Desk Reference, 2001 Edition. Specifically, the anti-inflammatory agent can include dexamethasone, which is chemically designated as (11β, 16α)-9-fluoro-11,17,21-trihydroxy-1,6-methylpregna-1,4-diene-3,20-dione. Alternatively, the anti-inflammatory agent can include sirolimus (rapamycin), which is a triene macrolide antibiotic isolated from Streptomyces hygroscopicus.

Anti-platelet or anti-coagulation agents include, e.g., Coumadin® (DuPont), Fragmin® (Pharmacia & Upjohn), Heparin® (Wyeth-Ayerst), Lovenox®, Normiflo®, Organan® (Organon), Aggrastat® (Merck), Agrylin®D (Roberts), Ecotrin® (Smithkline Beecham), Flolan® (Glaxo Wellcome), Halfprin® (Kramer), Integrillin® (COR Therapeutics), Integrillin® (Key), Persantine® (Boehringer Ingelheim), Plavix® (Bristol-Myers Squibb), ReoPro® (Centecor), Ticlid® (Roche), Abbokinase® (Abbtt), Activase® (Genentech), Eminase® (Roberts), and Strepase® (Astra). See, Physician's Desk Reference, 2001 Edition. Specifically, the anti-platelet or anti-coagulation agent can include trapidil (avantrin), cilostazol, heparin, hirudin, or ilprost.

Trapidil is chemically designated as N,N-dimethyl-5-methyl-[1,2,4]triazolo[1,-5-a]pyrimidin-7-amine.

Cilostazol is chemically designated as 6-[(1-cyclohexyl-1H-tetrazol-5-yl)-butoxy]-3,4-dihydro-2(1H)-quinolinone.

Heparin is a glycosaminoglycan with anticoagulant activity; a heterogeneous mixture of vatiably sulfonated polysaccharide chains composed of repeating units of D-glucosamine and either L-iduronic or D-glucuronic acids.

Hirudin is an anticoagulant protein extracted from leeches, e.g., Hirudo imiedicinalis.

Iloprost is chemically designated as 5-[Hexahydro-5-hydroxy-4-(3-hydroxy-4-methyl-1-octen-6-ynyl)-2(1H) pentalenylidene]pentanoic acid.

The immune suppressive agent can include, e.g., Azathioprine® (Roxane), BayRho-D® (Bayer Biological), CellCept® (Roche Laboratories), Imuran® ((Glaxo Wellcome), MiCRhoGAM® (Ortho-Clinical Diagnostics), Neoran® (Novartis), Orthoclone OKT3® (Ortho Biotech), Prograf® (Fujisawa), PhoGAM® (Ortho-Clinical Diagnostics), Sandimmune® (Novartis), Simulect® (Novartis), and Zenapax® (Roche Laboratories).

Specifically, the immune suppressive agent can include rapamycin or thalidomide.

Rapamycin is a triene macrolide isolated from *Streptomyces hygroscopicus.*

Thalidomide is chemically designated as 2-(2,6-dioxo-3-piperidinyl)-1H-iso-indole-1,3(2H)-dione.

Anti-cancer or anti-cell proliferation agents include, e.g., nucleotide and nucleoside analogs, such as 2-chloro-deoxyadenosine, adjunct antineoplastic agents, alkylating agents, nitrogen mustards, nitrosoureas, antibiotics, antimetabolites, hormonal agonists/antagonists, androgens, antiandrogens, antiestrogens, estrogen & nitrogen mustard combinations, gonadotropin releasing hotmone (GNRH) analogues, progestrins, immunomodulators, miscellaneous antineoplastics, photosensitizing agents, and skin & mucous membrane agents. See, *Physician's Desk Reference,* 2001 Edition.

Suitable adjunct antineoplastic agents include Anzemet® (Hoeschst Marion Roussel), Aredia® (Novartis), Didronel® (MGI), Diflucan® Pfizer), Epogen® (Amgen), Ergamisol® (Janssen), Ethyol® (Alza), Kytril® (SmithKline Beecham), Leucovorin® (Immunex), Leucovorin® (Glaxo Wellcome), Leucovorin® (Astra), Leukine®) (Immunex), Marinol® (Roxane), Mesnex® (Bristol-Myers Squibb Oncology/Immunology, Neupogen (Amgen), Procrit® (Ortho Biotech), Salagen®D (MGI), Sandostatin®D (Novartis), Zinecard® (Pharmacia & Upjohn), Zofran® (Glaxo Wellcome) and Zyloprim® (Glaxo Wellcome).

Suitable miscellaneous alkylating agents include Myleran® (Glaxo Wellcome), Paraplatin®D (Bristol-Myers Squibb Oncology/Immunology), Platinol® (Bristol-Myers Squibb Oncology/Immunology) and Thioplex® (Immunex).

Suitable nitrogen mustards include Alkeran® (Glaxo Wellcome), Cytoxan® (Bristol-Myers Squibb Oncology/Immunology), Ifex® (Bristol-Myers Squibb Oncology/Immunology), Leukeran® (Glaxo Wellcome) and Mustargen® (Merck).

Suitable nitrosoureas include BiCNU® (Bristol-Myers Squibb Oncology/Immunology), CeeNU® (Bristol-Myers Squibb Oncology/Immunology), Gliadel® (Rhône-Poulenc Rover) and Zanosar® (Pharmacia & Upjohn).

Suitable antibiotics include Adriamycin PFS/RDF® (Pharmacia & Upjohn), Blenoxane® (Bristol-Myers Squibb Oncology/Immunology), Cerubidine® (Bedford), Cosmegen® Merck), DaunoXome® (NeXstar), Doxil® (Sequus), Doxorubicin Hydrochloride® (Astra), Idamycin® PFS (Pharmacia & Upjohn), Mithracin® (Bayer), Mitamnycin® (Bristol-Myers Squibb Oncology/Immunology), Nipen®D (SuperGen), Novantrone® (Immunex) and Rubex® (Bristol-Myers Squibb Oncology/Immunology).

Suitable antimetabolites include Cytostar-U® (Pharmacia & Upjohn), Fludara®b (Berlex), Sterile FUDR® (Roche Laboratories), Leustatin® (Ortho Biotech), Methotrexate® (Immunex), Parinethol® (Glaxo Wellcome), Thioguanine® (Glaxo Wellcome) and Xeloda® (Roche Laboratories).

Suitable androgens include Nilandron® (Hoechst Marion Roussel) and Teslac® (Bristol-Myers Squibb Oncology/Immunology).

Suitable antiandrogens include Casodex® (Zeneca) and Eulexin® (Schering).

Suitable antiestrogens include Arimidex® (Zeneca), Fareston®g (Schering), Femara® (Novartis) and Nolvadex® (Zeneca).

Suitable estrogen & nitrogen mustard combinations include Emcyt® (Pharmacia & Upjohn).

Suitable estrogens include Estrace® (Bristol-Myers Squibb) and Estrab® (Solvay).

Suitable gonadotropin releasing hormone (GNRH) analogues include Leupron Depot® (TAP) and Zoladex®) (Zeneca).

Suitable progestins include Depo-Provera® (Pharmacia & Upjohn) and Megace® (Bristol-Myers Squibb Oncology/Immunology).

Suitable immunomodulators include Erganisol® (Janssen) and Proleukin® (Chiron Corporation).

Suitable miscellaneous antineoplastics include Camptosar® (Pharmacia & Upjohn), Celestone® (Schering), DTIC-Dome® (Bayer), Elspar® (Merck), Etopophos® (Bristol-Myers Squibb Oncology/Immunology), Etopoxide® (Astra), Gemzar® (Lilly), Hexalen® (U.S. Bioscience), Hycantin® (SmithKline Beecham), Hydrea® (Bristol-Myers Squibb Oncology/Immunology), Hydroxyurea® (Roxane), Intron A® (Schering), Lysodren® (Bristol-Myers Squibb Oncology/Immunology), Navelbine® (Glaxo Wellcome), Oncaspar® (Rhône-Poulenc Rover), Oncovin® (Lilly), Proleukin® (Chiron Corporation), Rituxan® (IDEC), Rituxan® (Genentech), Roferon-A® (Roche Laboratories), Taxol® (Bristol-Myers Squibb Oncology/Immunology), Taxotere® (Rhône-Poulenc Rover), TheraCys® (Pasteur Mérieux Connaught), Tice BCG® (Organon), Velban® (Lilly), VePesid® (Bristol-Myers Squibb Oncology/Immunology), Vesanoid® (Roche Laboratories) and Vumon® (Bristol-Myers Squibb Oncology/Immunology).

Suitable photosensitizing agents include Photofrin® (Sanofi).

Specifically, the anti-cancer or anti-cell proliferation agent can include Taxol® (paclitaxol), a niticoxide like compound, or NicOx (NCX-4016).

Taxol® (paclitaxol) is chemically designated as 5β,20-Epoxy-1,2α,4,7β,10β,13α-hexahydroxytax-11-en-9-one 4,10-acetate 2-benzoate 13-ester with (2R,3S)-N-benzoyl-3-phenylisoserine.

A niticoxide like compound includes any compound (e.g., polymer) to which is bound a nitric oxide releasing functional group. Suitable niticoxide like compounds are disclosed, e.g., in U.S. Pat. No. 5,650,447 and S-nitrosothiol derivative (adduct) of bovine or human serum albumin. See, e.g., *Inhibition of neointimal proliferation in rabbits after vascular injury by a single treatment with a protein adduct of nitric oxide*; David marks et al *J. Clin. Invest.* (1995); 96:2630-2638.

NCX-4016 is chemically designated as 2-acetoxy-benzoate 2-(nitroxymethyl)-phenyl ester, and is an antithrombitic agent.

It is appreciated that those skilled in the art understand that the drug useful in the present invention is the biologically active substance present in any of the drugs or agents disclosed above. For example, Taxol® (paclitaxol) is typically available as an injectable, slightly yellow, viscous solution. The drug, however, is a crystalline powder with the chemical name 5β,20-Epoxy-1,2α,4,7β,10β,13α-hexahydroxytax-11-en-9-one 4,10-diacetate 2-benzoate 13-ester with (2R,3S)-N-benzoyl-3-phenylisoserine. *Physician's Desk Reference* (PDR). Medical Economics Company (Montvale, N.J.), (53rd Ed.), pp. 1059-1067.

As used herein, a "residue of a drug" is a radical of a drug having one or more open valences. Any synthetically feasible atom or atoms of the drug can be removed to provide the open valence, provided bioactivity is substantially retained when the radical is attached to a residue of compound of formula (VII) or (XI). Based on the linkage that is desired, one skilled in the art can select suitably functionalized starting materials that can be derived from a drug using procedures that are known in the art.

The residue of a drug can be formed employing any suitable reagents and reaction conditions. Suitable reagents and reaction conditions are disclosed, e.g., in *Advanced Organic Chemistry, Part B: Reactions and Synthesis*, Second Edition, Carey and Sundberg (1983); *Advanced Organic Chemistry, Reactions Mechanisms, and Structure*, Second Edition, March (1977); and *Comprehensive Organic Transformations*, Second Edition, Larock (1999).

The polymer/drug linkage can degrade to provide a suitable and effective amount of drug. Any suitable and effective amount of drug can be released and will typically depend, e.g., on the specific polymer, drug, and polymer/drug linkage chosen. Typically, up to about 100% of the drug can be released from the polymer/drug. Specifically, up to about 90%, up to 75%, up to 50%, or up to 25% of the drug can be released from the polymer/drug. Factors that typically affect the amount of the drug that is released from the polymer/drug include, e.g., the nature and amount of polymer, the nature and amount of drug, the nature of the polymer/drug linkage, and the nature and amount of additional substances present in the formulation.

The polymer/drug linkage can degrade over a period of time to provide the suitable and effective amount of drug. Any suitable and effective period of time can be chosen. Typically, the suitable and effective amount of drug can be released in about twenty-four hours, in about seven days, in about thirty days, in about ninety days, or in about one hundred and twenty days. Factors that typically affect the length of time in which the drug is released from the polymer/drug include, e.g., the nature and amount of polymer, the nature and amount of drug, the nature of the polymer/drug linkage, and the nature and amount of additional substances present in the formulation.

Polymer/Linker/Drug Linkage

In addition to being directly linked to the residue of a compound of formula (VII) or (XI), the residue of a drug can also be linked to the residue of a compound of formula (VII) or (XI) by a suitable linker. The structure of the linker is not crucial, provided the resulting compound of the invention has an effective therapeutic index as a drug.

Suitable linkers include linkers that separate the residue of a compound of formula (VII) or (XI) and the residue of a drug by about 5 angstroms to about 200 angstroms, inclusive, in length. Other suitable linkers include linkers that separate the residue of a compound of formula (VII) or (I) and the residue of a drug by about 5 angstroms to about 100 angstroms, inclusive, in length, as well as linkers that separate the residue of a compound of formula (VII) or (XI) and the residue of a drug by about 5 angstroms to about 50 angstroms, or by about 5 angstroms to about 25 angstroms, inclusive, in length.

The linker can be linked to any synthetically feasible position on the residue of a compound of formula (VII) or (XI). Based on the linkage that is desired, one skilled in the art can select suitably functionalized starting materials that can be derived from a compound of formula (VII) or (XI) and a drug using procedures that are known in the art.

The linker can conveniently be linked to the residue of a compound of formula (VII) or (XI) or to the residue of a drug through an amide (e.g., —N(R)C(=O)— or —C(=O)N(R)—), ester (e.g., —OC(=O)— or —C(=O)O—), ether (e.g., —O—), ketone (e.g., —C(=O)—) thioether (e.g., —S—), sulfinyl (e.g., —S(O)—), sulfonyl (e.g., —S(O)$_2$—), disulfide (e.g., —S—S—), amino (e.g., —N(R)—) or a direct (e.g., C—C) linkage, wherein each R is independently H or (C$_1$-C$_6$)alkyl. The linkage can be formed from suitably functionalized starting materials using synthetic procedures that are known in the art. Based on the linkage that is desired, one skilled in the art can select suitably functional starting materials that can be derived from a residue of a compound of formula (VII) or (I), a residue of a drug, and from a given linker using procedures that are known in the art.

Specifically, the linker can be a divalent radical of the formula W-A-Q wherein A is (C$_1$-C$_{24}$)alkyl, (C$_2$-C$_{24}$)alkenyl, (C$_2$-C$_{24}$)alkynyl, (C$_3$-C$_8$)cycloalkyl, or (C$_6$-C$_{10}$)aryl wherein W and Q are each independently —N(R)C(=O)—, —C(=O)N(R)—, —OC(=O)—, —C(=O)O—, —O—, —S—, —S(O)—, —S(O)$_2$—, —S—S—, —N(R)—, C(=O)—, or a direct bond (i.e., W and/or Q is absent); wherein each R is independently H or (C$_1$-C$_6$)alkyl.

Specifically, the linker can be a divalent radical of the formula W—(CH$_2$)-Q wherein, n is between about 1 and about 20, between about 1 and about 15, between about 2 and about 10, between about 2 and about 6, or between about 4 and about 6; wherein W and Q are each independently —N(R)C(=O)—, —C(=O)N(R)—, —OC(=O)—, —C(=O)O—, —O—, —S—, —S(O)—, —S(O)$_2$—, —S—S—, —C(=O)—, —N(R)—, or a direct bond (i.e., W and/or Q is absent); wherein each R is independently H or (C$_1$-C$_6$)alkyl.

Specifically, W and Q can each independently be —N(R)C(=O)—, —C(=O)N(R)—, —OC(=O)—, —N(R)—, —C(=O)O—, —O—, or a direct bond (i.e., W and/or Q is absent).

Specifically, the linker can be a divalent radical formed from a saccharide.

Specifically, the linker can be a divalent radical formed from a cyclodextrin.

Specifically, the linker can be a divalent radical, i.e., 1,ω-divalent radicals formed from a peptide or an amino acid. The peptide can comprise 2 to about 25 amino acids, 2 to about 15 amino acids, or 2 to about 12 amino acids.

Specifically, the peptide can be poly-L-lysine (i.e., [—NHCH[(CH$_2$)$_4$NH$_2$]CO—]$_m$-Q, wherein Q is H, (C$_1$-C$_{14}$)alkyl, or a suitable carboxy protecting group; and wherein m is about 2 to about 25. Specifically, the poly-L-lysine can contain about 5 to about 15 residues (i.e., m is between about 5 and about 15). More specifically, the poly-L-lysine can contain about 8 to about 11 residues (i.e., m is between about 8 and about 11).

Specifically, the peptide can be poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-arginine, or poly-L-lysine-L-tyrosine.

Specifically, the linker can be prepared from 1,6-diaminohexane H$_2$N(CH$_2$)$_6$NH$_2$, 1,5-diaminopentane H$_2$N(CH$_2$)NH$_2$, 1,4-diaminobutane H$_2$N(CH$_2$)$_4$NH$_2$, or 1,3-diaminopropane H$_2$N(CH$_2$)$_3$NH$_2$.

One or more drugs can be linked to the polymer through a linker. Specifically, the residue of each of the drugs can each be linked to the residue of the polymer through a linker. Any suitable number of drugs (i.e., residues thereof) can be linked to the polymer (i.e., residue thereof) through a linker. The number of drugs that can be linked to the polymer, through a linker, can typically depend upon the molecular weight of the polymer. For example, for a compound of formula (VII), wherein n is about 50 to about 150, up to about 450 drugs (i.e., residues thereof) can be linked to the polymer (i.e., residue thereof) through a linker, up to about 300 drugs (i.e., residues thereof) can be linked to the polymer (i.e., residue thereof) through a linker, or up to about 150 drugs (i.e., residues thereof) can be linked to the polymer (i.e., residue thereof) through a linker. Likewise, for a compound of formula (XI), wherein n is about 50 to about 150, up to about 450 drugs (i.e., residues thereof) can be linked to the polymer (i.e., residue thereof) through a linker, up to about 300 drugs (i.e., residues thereof) can be linked to the polymer (i.e., residue thereof) through a linker, or up to about 150 drugs (i.e., residues thereof) can be linked to the polymer (i.e., residue thereof) through a linker.

In one embodiment of the present invention, a polymer (i.e., residue thereof) of the present invention can be linked to the linker via the carboxyl group (e.g., $COOR^2$) of the polymer. Specifically, a compound of formula (VII), wherein $R^2$ is independently hydrogen, or $(C_6$-$C_{10})$aryl$(C_1$-$C_6)$alkyl; a compound of formula (XI), wherein $R^2$ is independently hydrogen, or $(C_6$-$C_{10})$aryl$(C_1$-$C_6)$alkyl; or a combination thereof, can react with an amino functional group of the linker or a hydroxyl functional group of the linker, to provide a Polymer/Linker having an amide linkage or a Polymer/Linker having a carboxyl ester linkage, respectively. In another embodiment, the carboxyl group can be transformed into an acyl halide or an acyl anhydride.

In one embodiment of the present invention, a drug (i.e., residue thereof) can be linked to the linker via a carboxyl group (e.g., COOR, wherein R is hydrogen, $(C_6$-$C_{10})$aryl $(C_1$-$C_6)$alkyl or $(C_1$-$C_6)$alkyl) of the linker. Specifically, an amino functional group of the drug or a hydroxyl functional group of the drug can react with the carboxyl group of the linker, to provide a Linker/Drug having an amide linkage or a Linker/Drug having a carboxylic ester linkage, respectively. In another embodiment, the carboxyl group of the linker can be transformed into an acyl halide or an acyl anhydride.

The polymer/linker/drug linkage can degrade to provide a suitable and effective amount of drug. Any suitable and effective amount of drug can be released and will typically depend, e.g., on the specific polymer, drug, linker, and polymer/linker/drug linkage chosen. Typically, up to about 100% of the drug can be released from the polymer/linker/drug. Specifically, up to about 90%, up to 75%, up to 50%, or up to 25% of the drug can be released from the polymer/linker/drug. Factors that typically affect the amount of the drug that is released from the polymer/linker/drug include, e.g., the nature and amount of polymer, the nature and amount of drug, the nature and amount of linker, the nature of the polymer/linker/drug linkage, and the nature and amount of additional substances present in the formulation.

The polymer/linker/drug linkage can degrade over a period of time to provide the suitable and effective amount of drug. Any suitable and effective period of time can be chosen. Typically, the suitable and effective amount of drug can be released in about twenty-four hours, in about seven days, in about thirty days, in about ninety days, or in about one hundred and twenty days. Factors that typically affect the length of time in which the drug is released from the polymer/linker/drug include, e.g., the nature and amount of polymer, the nature and amount of drug, the nature of the linker, the nature of the polymer/linker/drug linkage, and the nature and amount of additional substances present in the formulation.

Polymer Intermixed with Drug

In addition to being linked to one or more drugs, either directly or through a linker, a polymer of the present invention can be physically intermixed with one or more drugs to provide a formulation.

As used herein, "intermixed" refers to a polymer of the present invention physically mixed with a drug or a polymer of the present invention physically in contact with a drug.

As used herein, a "formulation" refers to a polymer of the present invention intermixed with one or more drugs. The formulation includes a polymer of the present invention having one or more drugs present on the surface of the polymer, partially embedded in the polymer, or completely embedded in the polymer. Additionally, the formulation includes a polymer of the present invention and a drug forming a homogeneous composition (i.e., a homogeneous formulation).

Any suitable amount of polymer and drug can be employed to provide the formulation. The polymer can be present in about 0.1 wt. % to about 99.9 wt. % of the formulation. Typically, the polymer can be present above about 25 wt. % of the formulation; above about 50 wt. % of the formulation; above about 75 wt. % of the formulation; or above about 90 wt. % of the formulation. Likewise, the drug can be present in about 0.1 wt. % to about 99.9 wt. % of the formulation. Typically, the drug can be present above about 5 wt. % of the formulation; above about 10 wt. % of the formulation; above about 15 wt. % of the formulation; or above about 20 wt. % of the formulation.

The polymer/drug, polymer/linker/drug, formulation, or combination thereof can be applied, as a polymeric film, onto the surface of a medical device (e.g., stent). The surface of the medical device can be coated with the polymeric film. The polymeric film can have any suitable thickness on the medical device. For example, the thickness of the polymeric film on the medical device can be about 1 to about 50 microns thick or about 5 to about 20 microns thick. The polymeric film can effectively serve as a drug eluting polymeric coating. This drug eluting polymeric coating can be created by any suitable coating process, e.g., dip coating, vacuum depositing, or spray coating the polymeric film, on the medical device. Additionally, the drug eluting polymer coating system can be applied onto the surface of a stent, a vascular delivery catheter, a delivery balloon, a separate stent cover sheet configuration, or a stent drug delivery sleeves type of local drug delivery systems.

The drug eluting polymer coated stents can be used in conjunction with, e.g., hydrogel-based drug delivery systems.

In addition the above described polymer coated stent, various drugs mixed with hydrogels (see, U.S. Pat. No. 5,610,241) with different elution rate can be applied on the top of the polymer coated stent surface as a sandwich type of configuration to deliver anti restenotic agents to the blood vessels and prevent or reduce in-stent restenosis.

Any suitable size of polymer and drug can be employed to provide the formulation. For example, the polymer can have a size of less than about $1\times10^{-4}$ meters, less than about $1\times10^{-5}$ meters, less than about $1\times10^{-6}$ meters, less than about $1\times10^{-7}$ meters, less than about $1\times10^{-8}$ meters, or less than about $1\times10^{-9}$ meters.

The formulation can degrade to provide a suitable and effective amount of drug. Any suitable and effective amount of drug can be released and will typically depend, e.g., on the specific formulation chosen. Typically, up to about 100% of the drug can be released from the formulation. Specifically, up to about 90%, up to 75%, up to 50%, or up to 25% of the drug can be released from the formulation. Factors that typically affect the amount of the drug that is released from the formulation include, e.g., the nature and amount of polymer, the nature and amount of drug, and the nature and amount of additional substances present in the formulation.

The formulation can degrade over a period of time to provide the suitable and effective amount of drug. Any suitable and effective period of time can be chosen. Typically, the suitable and effective amount of drug can be released in about twenty-four hours, in about seven days, in about thirty days, in about ninety days, or in about one hundred and twenty days. Factors that typically affect the length of time in which the drug is released from the formulation include, e.g., the nature and amount of polymer, the nature and amount of drug, and the nature and amount of additional substances present in the formulation.

The present invention provides for a formulation that includes a polymer of the present invention physically intermixed with one or more drugs. The polymer that is present in the formulation can also be linked, either directly or through a linker, to one or more (e.g., 1, 2, 3, or 4) drugs. As such, a polymer of the present invention can be intermixed with one or more (e.g., 1, 2, 3, or 4) drugs and can be linked, either directly or through a linker, to one or more (e.g., 1, 2, 3, or 4) drugs.

A polymer of the present invention can include one or more drugs. In one embodiment, a polymer of the present invention can be physically intermixed with one or more drugs. In another embodiment, a polymer of the present invention can be linked to one or more drugs, either directly or through a linker. In another embodiment, a polymer of the present invention can be linked to one or more drugs, either directly or through a linker, and the resulting polymer can be physically intermixed with one or more drugs.

A polymer of the present invention, whether or not present in a formulation as described herein, whether or not linked to a drug as described herein, and whether or not intermixed with a drug as described herein, can be used in medical therapy or medical diagnosis. For example, the polymer can be used in the manufacture of a medical device. Suitable medical devices include, e.g., artificial joints, artificial bones, cardiovascular medical devices, stents, shunts, medical devices useful in angioplastic therapy, artificial heart valves, artificial by-passes, sutures, artificial arteries, a vascular delivery catheters, a delivery balloons, separate stent cover sheet configurations, and stent drug delivery sleeve types of local drug delivery systems.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The present invention will now be illustrated by the following non-limiting examples.

EXAMPLES

Preparation of copoly(ester amide)s (coPEAs) and copoly (ester urethane)s (coPEURs) (general procedure)

Dry triethylamine (Net) (30.8 mL, 0.22 mole) was added to a mixture of predetermined quantities of the di-p-toluenesulfonic acid salt of bis-(L-α-amino acid)α,ω-alkylene diester (III) and the di-p-toluenesulfonic acid salt of L-lysine benzyl ester (IV) (total amount of (III)+(IV)=0.1 mole), and active diester (V) or active bis-carbonate (IV) (0.1 mole) in dry N,N-dimethylacetamide (DMA) (52.5 mL) (total volume of DMA and $NEt_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into cool water. The separated polymer was thoroughly washed with water, dried at about 30° C. under reduced pressure (for final purification of coPEAs and coPEURs see below). Reduced viscosity data ($\eta_{red}$) of the polymers were obtained in m-cresol at a concentration of 0.5 g/dL and t=25° C.

Preparation of CoPEAs:

Example 1

Preparation of co-poly-{[N,N'-adipoyl-bis-(L-leucine)-1,6-hexylene diester]$_{0.75}$-{[N,N'-adipoyl-L-lysine benzyl ester]$_{0.25}$} (1) (compound of formula (VII) wherein m=0.75, p=0.25, n=75, $R_1$=$(CH_2)_4$, $R_2$=Bz, $R_3$=iso-propyl and $R_4$=$(CH_2)_6$).

Dry triethylamine (30.8 mL, 0.22 mole) was added to the mixture of the di-p-toluenesulfonic acid salt of bis-(L-leucine)-1,6-hexylene diester (III, $R^4$ $(CH_2)_6$) (50.168 g, 0.075 mole); the di-p-toluenesulfonic acid salt of L-lysine benzyl ester (IV) (total amount of (III)+(IV)=0.1 mole) (14.518 g, 0.025 mole); and di-p-nitrophenyl adipate (V, $R^1$=$(CH_2)_4$) (38.833 g, 0.1 mole) in dry N,N-dimethylacetamide (52.5 mL) (total volume of DMA and $NEt_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below), yield is 90%, $\eta_{red}$=1.30 dL/g. Mw=32,100, Mn=27,000, Mw/Mn=1.19 (GPC in THF).

Example 2

Preparation of co-poly-{[N,N'-sebacoyl-bis-(L-leucine)-1,6-hexylene diester]$_{0.75}$-{[N,N'-sebacoyl-L-lysine benzyl ester]$_{0.25}$} (2) (compound of formula (VII) wherein m=0.75, p=0.25, n=65, $R_1$=$(CH_2)_8$, $R_2$=Bz, $R_3$=iso-propyl, and $R_4$=$(CH_2)_6$).

Dry triethylamine (30.8 mL, 0.22 mole) was added to the mixture of di-p-toluenesulfonic acid salt of bis-(L-leucine)-1,6-hexylene diester (III, $R^4$=$(CH_2)_6$) (50.168 g (0.075 mole); the di-p-toluenesulfonic acid salt of L-lysine benzyl ester (IV) (14.518 g, 0.025 mole) (total amount of (III)+(IV)=0.1 mole), and di-p-nitrophenyl sebacinate (V, $R^1$=$(CH_2)_8$) (44.444 g, 0.1 mole) in dry N,N-dimethylacetamide (DMA) (52.5 mL) (total volume of DMA and $NEt_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below), yield is 91%, $\eta_{red}$=1.40 dL/g. Mw=31.300, Mn=21.000, Mw/Mn=1.49 (GPC in THF). Biodegradation (weight loss in %) at 37° C. after 120 h in phosphate buffer (pH 7.4): ~0% weight loss in pure buffer, 1-2% in the buffer with α-chymotrypsin (4 mg/10 mL of buffer), 1-2% in the buffer with lipase (4 mg/10 mL of buffer).

Example 3

Preparation of co-poly-{[N,N'-adipoyl-bis-(L-leucine)1,6-hexylene diester]}$_{0.50}$-[N,N'-adipoyl-bis-(L-phenylalanine)-1,6-hexylene diester]$_{0.25}$-{[N,N'-adipoyl-L-lysine benzyl ester]$_{0.25}$} (3) (compound of formula (VII) wherein m=0.50, p=0.50, $R_1$=(CH$_2$)$_4$, $R_2$=Bz, $R_3$=iso-propyl and Bz, and $R_4$=(CH$_2$)$_6$ and Bz).

Dry triethylamine (30.8 mL, 0.22 mole) was added to the mixture of the di-p-toluenesulfonic acid salt of bis-(L-leucine)-1,6-hexylene diester (III, $R^4$ (CH$_2$)$_6$) (34.446 g, 0.050 mole), the di-p-toluenesulfonic acid salt of bis-(L-phenylalanine)1,6-hexylene diester (III, $R^4$=CH$_2$Ph) (18.924 g, 0.025 mole), the di-p-toluenesulfonic acid salt of L-lysine benzyl ester (IV) (14.5180 g, 0.025 mole) (total amount of (III)+(IV)=0.1 mole), and di-p-nitrophenyl adipate (V, $R^1$=(CH$_2$)$_4$) (38.833, 0.1 mole) in dry N,N-dimethylacetamide (DMA) (52.5 mL of) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below), yield is 94%, $\eta_{red}$=1.40 dL/g. Biodegradation (weight loss in %) at 37° C. after 120 h in phosphate buffer (pH 7.4): ~0% in pure buffer, 10% in the buffer with α-chymotrypsin (4 mg/10 mL of buffer), and 35% in the buffer with lipase (4 mg/10 mL of buffer).

Example 4

Preparation of co-poly-{[N,N'-sebacoyl-bis-(L-leucine)-1,6-hexylene diester]}$_{0.50}$-[N,N'-sebacoyl-(bis-(L-phenylalanine)-1,6-hexylene diester]$_{0.25}$-{[N,N'-sebacoyl-L-lysine benzyl ester]$_{0.25}$} (4) (compound of formula (VII) wherein $m^1$=0.50, $m^2$=0.25, p=0.25, $R_1$=(CH$_2$)$_8$, $R_2$=Bz, $R_3$=iso-propyl, and $R_4$=(CH$_2$)$_6$).

Dry triethylamine (30.8 mL, 0.22 mole) was added to the mixture of the of di-p-toluenesulfonic acid salt of bis-(L-leucine)-1,6-hexylene diester (III, $R^4$=(CH$_2$)$_6$) (34.446 g, 0.050 mole), the di-p-toluenesulfonic acid salt of bis-(L-phenylalanine)1,6-hexylene diester (III, $R^4$=CH$_2$Ph) (18.924 g, 0.025 mole), the di-p-toluenesulfonic acid salt of L-lysine benzyl ester (IV) (14.518 g, 0.025 mole) (total amount of (III)+(IV)=0.1 mole), and di-p-nitrophenyl sebacinate (V, $R_1$=CH$_2$)$_8$) (44.444 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 95%, $\eta_{red}$=0.77 dL/g. Tg=20.6° C. (DSC).

Example 5

Preparation of co-poly-{[N,N'-adipoyl-bis-(L-leucine)-1,6-hexylene diester]}$_{0.50}$-{[N,N'-adipoyl-L-lysine benzyl ester]$_{0.50}$} (5) (compound of formula (VII) wherein m=0.50, p=0.50, $R_1$=((CH$_2$))$_4$, $R_2$=Bz, $R_3$=iso-propyl, and 4=(CH$_2$)).

Dry triethylamine (30.8 mL, 0.22 mole) was added to the mixture of the di-p-toluenesulfonic acid salt of bis-(L-leucine)-1,6-hexylene diester (III, $R^4$=(CH$_2$)$_6$) (34.446 g, 0.050 mole), the di-p-toluenesulfonic acid salt of L-lysine benzyl ester (IV) (29.036 g, 0.050 mole) (total amount of (III)+(IV)=0.1 mole), and di-p-nitrophenyl adipate (V, $R^1$=(CH$_2$)$_4$) (38.833 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 93%, $\eta_{red}$=1.25 dL/g.

Example 6

Preparation of co-poly-{[N,N'-sebacoyl-bis-(L-leucine)-1,6-hexylene diester]}$_{0.50}$-{[N,N'-sebacoyl-L-lysine benzyl ester]$_{0.50}$} (6) (compound of formula (VII) wherein m=0.50, p=0.50, $R_1$=(CH$_2$)$_8$, $R_2$=Bz, $R_3$=iso-propyl, and $R_4$=(CH$_2$)$_6$).

Dry triethylamine (30.8 mL, 0.22 mole) was added to the mixture of the di-p-toluenesulfonic acid salt of bis-(L-leucine)-1,6-hexylene diester (E, $R^4$=(CH$_2$)$_6$) (34.446 g, 0.050 mole), the di-p-toluenesulfonic acid salt of L-lysine benzyl ester (IV) (29.036 g, 0.050 mole) (total amount of (III)+(IV)=0.1 mole), and di-p-nitrophenyl sebacinate (V, $R^1$=(CH$_2$)$_8$ (44.444 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 95%, $\eta_{red}$=1.31 dL/g.

Example 7

Preparation of co-poly-{[N,N'-adipoyl-bis-(L-leucine)1,8-octylene diester]}$_{0.90}$-{[N,N'-adipoyl-L-lysine benzyl ester]$_{0.10}$} (7) (compound of formula (VII) wherein m=0.90, p=0.10, $R_1$=(CH$_2$)$_4$, $R_2$=Bz, $R_3$=iso-propyl, and $R_4$=(CH$_2$)$_8$).

Dry triethylamine (30.8 mL, 0.22 mole) was added to the mixture of the di-p-toluenesulfonic acid salt of bis-(L-leucine)-1,8-octylene diester (III, $R^4$=(CH$_2$)$_8$) (64.526 g, 0.090 mole), the di-p-toluenesulfonic acid salt of L-lysine benzyl ester (IV) (5.807 g, 0.010 mole) (total amount of (III)+(IV)=0.1 mole), and di-p-nitrophenyl adipate (V, $R^1$=(CH$_2$)$_4$) (38.833, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at

Example 8

Preparation of co-poly-{[N,N'-sebacoyl-bis-(L-leucine)-1,4-butylene diester]}$_{0.09}$-{[N,N'-sebacoyl-L-lysine benzyl ester]$_{0.10}$} (8) (compound of formula (Vet) wherein m=0.90, p=0.10, R$_1$=(CH$_2$)$_8$, R$_2$=Bz, R$_3$=iso-propyl, and R$_4$ (CH$_{2)4}$).

Dry triethylamine (30.8 mL, 0.22 mole) was added to the mixture of the di-p-toluenesulfonic acid salt of bis-(L-leucine)-1,4-butylene diester (III, R$^4$=(CH$_2$)$_4$) (59.477 g, 0.090 mole), the di-p-toluenesulfonic acid salt of L-lysine benzyl ester (IV) (5.807 g, 0.010 mole) (total amount of (III)+(IV)=0.1 mole), and di-p-nitrophenyl sebacinate (V, R$^1$=(CH$_2$)$_8$) (44.444 g, 0.1 mole) in dry N,N -dimethylacetamide (DMA) (52.5 mL of) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at 30° C. under reduced pressure. After final purification up to negative test on p-nitrophenol and p-toluenesulfonic acid (see below) yield is 95%, η$_{red}$=1.28 dL/g.

Example 9

Preparation of co-poly-{[N,N'-sebacoyl-bis-(L-leucine)-1,6-hexylene diester])}$_{0.90}$-{[N,N'-sebacoyl-L-lysine benzyl ester]$_{0.10}$} (9) (compound of formula (VII) wherein m=0.90, p=0.10, R$_1$=(CH$_2$)$_8$, R$_2$=Bz, R$_3$=iso-propyl, and R$_4$=(C$_2$)$_6$).

Dry triethylamine (30.8 mL, 0.22 mole) was added to the mixture of the di-p-toluenesulfonic acid salt of bis-(L-leucine)-1,6-hexylene diester (III, R$^4$=(CH$_2$)$_6$) (62.002 g, 0.090 mole), the di-p-toluenesulfonic acid salt of L-lysine benzyl ester (IV) (5.807 g, 0.010 mole) (total amount of (III)+(IV)=0.1 mole), and di-p-nitrophenyl sebacinate (V, R$^1$=(C$_2$)$_8$) (44.444 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 96%, η$_{red}$=1.41 dL/g. Biodegradation (weight loss in %) at 37° C. after 120 h in phosphate buffer (pH 7.4): ~0% in pure buffer, 12% in the buffer with α-chymotrypsin (4 mg/10 mL of buffer), and 38% in the buffer with lipase (4 mg/10 mL of buffer).

Example 10

Preparation of co-poly-{[N,N'-sebacoyl-bis-(L-leucine)-1,8-octylene diester]}$_{0.90}$-{[N,N'-sebacoyl-L-lysine benzyl ester]$_{0.10}$} (10) (compound of formula (VII) wherein m=$_{0.90}$, p=$_{0.10}$, R$_1$=(CH$_2$)$_8$, R$_2$=Bz, R$_3$=iso-propyl, and R$_4$=(C$_2$)$_8$.

Dry triethylamine (30.8 mL, 0.22 mole) was added to the mixture of the di-p-toluenesulfonic acid salt of bis-(L-leucine)-1,8-octylene diester (III, R$^4$=(CH$_2$)$_8$) (64.526 g, 0.090 mole), the di-p-toluenesulfonic acid salt of L-lysine benzyl ester (IV) (5.807 g, 0.010 mole) (total amount of (III)+(IV)=0.1 mole), and di-p-nitrophenyl sebacinate (V, R$^1$=(CH$_2$)$_8$) (44.444 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification up to negative test on p-nitrophenol and p-toluenesulfonic acid (see below) yield is 97%, η$_{red}$=1.50 dL/g. Tg 27.5° C. (DSC).

Example 11

Preparation of co-poly-{[N,N'-sebacoyl-bis-(L-leucine)-1,12-dodecylene diester]}$_{0.90}$-{[N,N'-sebacoyl-L-lysine benzyl ester]$_{0.10}$} (11) (compound of formula (VII) wherein m=0.90, p=0.10, R$_1$=(CH$_2$)$_8$, R$_2$=Bz, R$_3$=iso-propyl, and R$_4$=(CH$_2$)$_{12}$).

Dry triethylamine (30.8 mL, 0.22 mole) was added to the mixture of the di-p-toluenesulfonic acid salt of bis-(L-leucine)-1,12-dodecylene diester (III, R$^4$=(CH$_2$)12) (69.576 g, 0.090 mole), the di-p-toluenesulfonic acid salt of L-lysine benzyl ester (IV) (5.807 g, 0.010 mole) (total amount of (III)+(IV) 0.1 mole), and di-p-nitrophenyl sebacinate (V, R$^1$=(CH$_2$)$_8$) (44.444 g, 0.1 mole) in dry N,N-dimethylacetamide (DMA) (52.5 mL) (total volume of DMA and NEt$_3$ is 83.3 mL, concentration 1.2 mol/L by (III)+(IV) or by (V)) at room temperature. Afterwards, the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at about 30° C. under reduced pressure. After final purification, yield is 96% up to negative test on p-nitrophenol and p-toluenesulfonic acid (see below), η$_{red}$=0.68 dL/g.

Example 12

Preparation of co-poly-{[N,N'-dodecyldicarboxyloyl-bis-(L-leucine)-1,6-hexylene diester]}$_{0.90}$-{[N,N'-dodecyldicarboxyloyl-L-lysine benzyl ester]$_{0.10}$} (12) (compound of formula (VII) wherein m=0.90, p=0.10, R$_1$=(CH$_2$)$_{12}$, R$_2$=Bz, R$_3$=iso-propyl, and R$_4$=(CH$_2$)$_6$).

Dry triethylamine (30.8 mL, 0.22 mole) was added to the mixture of the di-p-toluenesulfonic acid salt of bis-(L-leucine)-1,6-hexylene diester (III, R$^4$=(CH$_2$)$_6$) (62.002 g, 0.090 mole), the di-p-toluenesulfonic acid salt of L-lysine benzyl ester (IV) (5.807 g, 0.010 mole) (total amount of (III)+(IV)=0.1 mole), and di-p-nitrophenyl dodecyldicarboxylate (V, R$^1$=(CH$_2$)$_{12}$)(50.055 g, 0.1 mole) in dry N,N-dimethylacetamide (DMA) (52.5 mL) (total volume of DMA and NEt$_3$ in 83.3 mL, concentration 1.2 mol/L by (III)+(IV) or by (V)) at room temperature. Afterwards the temperature of the reaction mixture was increased to about 80° C. and stirred for about 16 hours. The viscous reaction solution was cooled to room temperature, diluted with ethanol (150 mL), and poured into water. The separated polymer was thoroughly washed with water, dried at 30° C. under reduced pressure. After final purification yield is 96% up to negative test on p-nitrophenol and p-toluenesulfonic acid (see below), $\eta_{red}$=1.18 dL/g.

Preparation of Co-PEURs:

Example 13

Preparation of co-poly-{[N,N'-trimethylenedioxydicarbonyl-bis-(L-leucine)1,4-butylene diester]}$_{0.75}$-{[N,N'-trimethylenedioxydicarbonyl-L-lysine benzyl ester]$_{0.25}$} (13) (compound of formula (XI) wherein m=0.75, p=0.25, $R_2$=Bz, $R_3$=iso-propyl, $R_4$=$(CH_2)_4$), and $R_6$=$(CH_2)_3$.

Dry triethylamine (30.8 mL, 0.22 mole) was added to the mixture of the di-p-toluenesulfonic acid salt of bis-(L-leucine)-1,4-butylene diester ([H, $R^4$=$(CH_2)_4$) (49.565 g, 0.075 mole), the di-p-toluenesulfonic acid salt of L-lysine benzyl ester (V) (14.518 g, 0.025 mole) (total amount of (III)+(IV)=0.1 mole), and active bis-carbonate (X) ($R^6$=$(CH_2)_3$) (40.624 g, 0.1 mole) in dry N,N-dimethylacetamide DMA) (52.5 mL) (total volume of DMA and $NEt_3$ in 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at 30° C. under reduced pressure. After final purification up to negative test on p-nitrophenol and p-toluenesulfonic acid (see below) yield is 63%, $\eta_{red}$=0.32 dL/g.

Example 14

Preparation of co-poly-{[N,N'-(3-oxapentylene-1,5-dioxydicarbonyl)bis-(L-leucine)-1,4-butylene diester]}$_{0.75}$-{[N,N'-(3-oxapentylene-1,5-dioxydicarbonyl)-L-lysine benzyl ester]$_{0.25}$} (14) (compound of formula (XI) wherein m=0.75, p=0.25, $R_2$=Bz, $R_3$=iso-propyl, $R_4$=$(CH_2)_4$), and $R_6$=$(CH_2)_2$—O—$(CH_2)_2$)

Dry triethylamine (30.8 mL, 0.22 mole) was added to the mixture of the di-p-toluenesulfonic acid salt of bis-(L-leucine)-1,4-butylene diester (III, $R^4$=$(CH_2)_4$) (49.565 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) ($R^6$=$(CH_2)_2$—O—$(CH_2)_2$) (43.633 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 78%, $\eta_{red}$=0.58 dL/g. Biodegradation (weight loss in %) at 37° C. after 240 h in phosphate buffer (pH 7.4): 4.7% in pure buffer, 2.2% in the buffer with α-chymotrypsin (4 mg/10 mL of buffer), 4.4% in the buffer with lipase (4 mg/10 mL of buffer). Films with d=4 cm and m=500±50 mg on Teflon backing.

Example 15

Preparation of co-poly-{[N,N'-trimethylenedioxydicarbonyl-bis-(L-leucine)-1,6-hexylene diester]}$_{0.75}$-{[N,N'-trimethylenedioxydicarbonyl-L-lysine benzyl ester]$_{0.25}$} (15) (compound of formula (XI) wherein m=0.75, p=0.25, n=112, $R_2$=Bz, $R_3$=iso-propyl, $R_4$=$(CH_2)_6$, and $R_4$=$(CH_2)_3$.

Dry triethylamine (30.8 mL, 0.22 mole) was added to the mixture of the di-p-toluenesulfonic acid salt of bis-(L-leucine)-1,6-hexylene diester (III, $R^4$=$(CH_2)_6$) (51.668 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) ($R^6$=$(CH_2)_3$) (40.624 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 60%, $\eta_{red}$=0.53 dL/g. Mw=50,000, Mn=29,900, $M_w/M_n$=1.68 (GPC). Biodegradation (weight loss in %) at 37° C. after 180 h in phosphate buffer (pH 7.4): 5.0% in pure buffer, 7.3% in the buffer with α-chymotrypsin (4 mg/10 mL of buffer), and 8.2% in the buffer with lipase (4 mg/10 mL of buffer). Films with d=4 cm and m=500±50 mg on Teflon backing.

Example 16

Preparation of co-poly-{[N,N'-(3-oxapentylene-1,5-dioxydicarbonyl)-bis-(L-leucine)-1,6-hexylene diester]}$_{0.75}$-{[N,N'-(3-oxapentylene-1,5-dioxydicarbonyl)L-lysine benzyl ester]$_{0.25}$} (16) (compound of formula (XI) wherein m=0.75, p=0.25, n=130, $R_2$=Bz, $R_3$=iso-propyl, $R_4$=$(CH_2)_6$), and $R_6$=$(CH_2)_2$—O—$(CH_2)_2$)

Dry triethylamine (30.8 mL, 0.22 mole) was added to the mixture of the di-p-toluenesulfonic acid salt of bis-(L-leucine)-1,6-hexylene diester (III, $R^4$=$(CH_2)_6$) (51.668 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) ($R^6$=$(CH_2)_2$—O—$(CH_2)_2$) (43.633 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 68%, $\eta_{red}$=0.72 dL/g. Mw=61,900, n=38,500, Mw/Mn=1.61 (GPC). Biodegradation (weight loss in %) at 37° C. after 180 h in phosphate buffer (pH 7.4): 4.0% in pure buffer, 5.6% in the buffer with α-chymotrypsin (4 mg/10 mL of buffer), and 8.9% in the buffer with lipase (4 mg/10 mL of buffer). Films with d=4 cm and m=500±50 mg on Teflon backing.

Example 17

Preparation of co-poly-{[N,N'-(3-oxapentylene-1,5-dioxydicarbonyl)-bis-(L-leucine)-1,6-hexylene diester]}$_{0.50}$-{

[N,N'-(3-oxapentylene-1,5-dioxydicarbonyl)-L-lysine benzyl ester]$_{0.50}$} (17) (compound of formula (XI) wherein m=0.50, p=0.50, n=85, $R_2$=Bz, $R_3$=iso-propyl, $R_4$=$(CH_2)_6$), and $R_6$=$(CH_2)_2$—O—$(CH_2)_2$).

Dry triethylamine (30.8 mL, 0.22 mole) was added to the mixture of di-p-toluenesulfonic acid salt of bis-(L-leucine)-1,6-hexylene diester (III, $R^4$=$(CH_2)_6$) (34.446 g, 0.050 mole), the di-p-toluenesulfonic acid salt of L-lysine benzyl ester (IV) (29.036 g, 0.050 mole) (total amount of (III)+(IV)=0.1 mole), and active bis-carbonate (X) ($R^6$=$(CH_2)_2$—O—$(CH_2)_2$) (43.633 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 80%, $\eta_{red}$=0.45 dL/g. $M_w$=37,900, $M_n$=22,300, Mw/Mn=1.70 (GPC).

Example 18

Preparation of co-poly-{[N,N'-(3-oxapentylene-1,5-dioxydicarbonyl)-bis-(L-leucine)-1,6-hexylene diester]}$_{0.90}$-{[N,N'-(3-oxapentylene-1,5-dioxydicarbonyl)-L-lysine benzyl ester]$_{0.10}$} (18) (compound of formula (XI) wherein m=0.90, p=0.10, n=115, $R_2$=Bz, $R_3$=iso-propyl, $R_4$=$(CH_2)_6$), and $R_6$=$(C_2)_2$—O—$(CH_2)_2$).

Dry triethylamine (30.8 mL, 0.22 mole) was added to the mixture of the di-p-toluenesulfonic acid salt of bis-(L-leucine)-1,6-hexylene diester (III, $R^4$=$(CH_2)_6$) (62.002 g, 0.090 mole), the di-p-toluenesulfonic acid salt of L-lysine benzyl ester (IV) (5.807 g, 0.025 mole) (total amount of (III)+(IV)=0.1 mole), and active bis-carbonate (X) ($R^6$=$(CH_2)_2$—O—$(CH_2)_2$) (43.633 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 70%, $\eta_{red}$=0.74 dL/g. $M_w$=56,500, $M_n$=33,700, $M_w/M_n$=1.68 (GPC).

Example 19

Preparation of co-poly-{[N,N'-trimethylenedioxydicarbonyl-bis-(L-leucine)-1,8-octylene diester]}$_{0.75}$-{N,N'-trimethylenedioxydicarbonyl-L-lysine benzyl ester]$_{0.25}$} (19) (compound of formula (XI) wherein m=0.75, p=0.25, $R_2$=Bz, $R_3$=iso-propyl, $R_4$=$(CH_2)_8$), and $R_6$=$(CH_2)_3$.

Dry triethylamine (30.8 mL, 0.22 mole) was added to the mixture of the di-p-toluenesulfonic acid salt of bis-(L-leucine)-1,8-octylene diester (III, $R^4$=$(CH_2)_8$) (53.772 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) ($R^6$=$(CH_{2)3}$) (40.624 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards, the temperature of the reaction mixture was increased to about 80° C. and stirred for about 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 84%, $\eta_{red}$=0.46 dL/g. Biodegradation (weight loss in %) at 37° C. after 240 h in phosphate buffer (pH 7.4): 0.9% in pure buffer, 2.0% in the buffer with a-chymotrypsin (4 mg/10 mL of buffer), and 3.7% in the buffer with lipase (4 mg/0 mL of buffer). Films with d=4 cm and m=500±50 mg on Teflon backing.

Example 20

Preparation of co-poly-{[N,N'-(3-oxapentylene-1,5-dioxydicarbonyl)-bis-(L-leucine)-1,8-octylene diester]}$_{0.75}$-{[N,N'-(3-oxapentylene-1,5-dioxydicarbonyl)-L-lysine benzyl ester]$_{0.25}$} (20) (compound of formula (XI) wherein m=0.75, p=0.25, $R_2$=Bz, $R_3$=iso-propyl, $R_4$=$(CH_2)_8$), and $R_6$=$(CH_2)_2$—O—$(CH_2)_2$).

Dry triethylamine (30.8 mL, 0.22 mole) was added to the mixture of the di-p-toluenesulfonic acid salt of bis-(L-leucine)-1,8-octylene diester (III, $R_4$=$(CH_2)_8$) (53.772 g, 0.075 mole), the di-p-toluenesulfonic acid salt of L-lysine benzyl ester (IV) (14.518 g, 0.025 mole) (total amount of (III)+(IV)=0.1 mole), and active bis-carbonate (X) $R^6$=$(CH_2)_2$—$(CH_2)_2$(43.63 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards the temperature of the reaction mixture was increased to about 80° C. and stirred for 16 hours. The viscous reaction solution was cooled to room temperature, and poured into water. The separated polymer was thoroughly washed with water, dried at about 30° C. under reduced pressure. After final purification, yield is 76% up to negative test on p-nitrophenol and p-toluenesulfonic acid (see below), $\eta_{red}$=0.42 dL/g.

Example 21

Preparation of co-poly-{[N,N'-(3-oxapentylene-1,5-dioxydicarbonyl)-bis-(L-leucine)-1,8-octylene diester]}$_{0.90}$-{[N,N'-(3-oxapentylene-1,5-dioxydicarbonyl)-L-lysine benzyl ester]$_{0.10}$} (21) (compound of formula (XI) wherein m=0.90, p=0.10, $R_2$=Bz, $R_3$=iso-propyl, $R_4$=$(CH_2)_8$), and $R_6$=$(CH_2)_2$—O—$(CH_2)_2$).

Dry triethylamine (30.8 mL, 0.22 mole) was added to the mixture of the di-p-toluenesulfonic acid salt of bis-(L-leucine)-1,8-octylene diester (III, $R^4$=$(C_2)_8$) (64.5264 g, 0.09 mole), the di-p-toluenesulfonic acid salt of L-lysine benzyl ester (IV) (5.8072 g, 0.01 mole) (total amount of (III)+(IV)=0.1 mole), and active bis-carbonate (X) ($R^6$=$(CH_2)_2$—O—$(CH_2)_2$) (43.63 g, 0.1 mole) in dry N,N-dimethylacetamide (DMA) (52.5 mL) (total volume of DMA and $NEt_3$ is 83.3 mL, concentration 1.2 mol/L by (III)+(IV) or by (X)) at room temperature. Afterwards the temperature of the reaction mixture was increased to about 80° C. and stirred for 16 hours. The viscous reaction solution was cooled to room temperature, and poured into water. The separated polymer was thoroughly washed with water, dried at about 30° C. under reduced pressure. After final purification up to negative test on p-nitrophenol and p-toluenesulfonic acid (see below) yield is 63%, $\eta_{red}$=0.51 dL/g.

Example 22

Deprotection of Polymeric Benzyl Esters (General Procedure)

According to the general procedure described herein for the preparation of coPEAs and coPEURs, the polymers were obtained as the benzyl ester forms. For the preparation of the corresponding polymers having free COOH groups, these polymers having the benzyl esters were subjected to catalytic debenzylation using hydrogen ($H_2$) gas and palladium (Pd) black as a catalyst. Suitable reaction conditions are available, e.g., in T. W. Greene, *Protecting Groups In Organic Synthesis*; Wiley: New York, 1981; J. March, *Advanced Organic Chemistry. Reactions, Mechanisms and Structure*, (2nd Ed.), McGraw Hill: New York, 1977; F. Carey and R. Sundberg, *Advanced Organic Chemistry Part B: Reactions and Synthesis*, (2nd Ed.), Plenum: New York, 1977; and references cited therein.

(A.) Deprotection of Polymeric Benzyl Esters (coPEAs)

Palladium black catalyst (3.0 g) was added to a solution of the polymer (benzyl ester form) (10 g) in ethanol (100 mL), and dry gaseous hydrogen was bubbled through the solution for about 10 hours to about 20 hours. A magnetic stirrer was used to agitate the solution. After catalytic hydrogenolysis was complete, the reaction mixture was filtered, and clear and colorless solutions were obtained.

(B.) Deprotection of Polymeric Benzyl Esters (coPEURs)

Palladium black catalyst (3.0 g) was added to a solution of the polymer (benzyl ester form) (10 g) in ethyl acetate (100 mL), and dry gaseous hydrogen was bubbled through the solution for about 10 hours to about 30 hours. A magnetic stirrer was used to agitate the solution. After catalytic hydrogenolysis was complete, the reaction mixture was filtered, and clear and colorless solutions were obtained After deprotection of the polymers, no substantial change of molecular weight or polydispersity was observed. For example, for the compound (2) from Table 3 (i.e., benzyl ester form) the molecular weight characteristics were as follows: Mw=31.300, Mn=21.000, Mw/Mn=1.49. After hydrogenolysis, molecular weight characteristics are: Mw=40.900, Mn=28.000, and Mw/$M_n$=1.46.

Example 23

Purification of the Benzyl Ester Polymers (General Procedures)

After the polymers were precipitated in water and thoroughly washed with water, the solvent (DMA) and p-toluenesulfonic acid salt of triethylamine were removed (nearly to completion). However, the polymers still contain a significant amount of by-product of the polycondensation (e.g., p-nitrophenol) which was removed as described below.

(A.) Purification of coPEAs

The polymer obtained above (10 g) was dissolved in ethanol (50 mL, 95%). The solution was filtered and the polymer was precipitated in ethyl acetate (1.0 L), where it separates as tar like mass, and was kept overnight in refrigerator. The ethyl acetate was removed and a fresh portion of ethyl acetate (1.0 L) was added to the tar like mass and kept overnight in refrigerator again. This procedure was repeated until a negative test on p-nitrophenol (see below) was obtained. Normally it was repeated for 1-2 times. After such a treatment, p-nitrophenol (which is more soluble in ethylacetate than in water), was nearly completely removed from the polymers. The obtained tar like mass was dried, dissolved in 95% ethanol, precipitated in distilled water as a rubber-like mass, and dried at about 60° C. under reduced pressure. Yields of purified coPEAs were up to about 97%.

(B.) Purification of coPEURs

The polymer obtained above (10 g) was dissolved in chloroform (100 mL), cast as a thin film onto a cylindrical glass vessel's (d=400-500 mm) inner surface, dried at room temperature, thoroughly washed with water, and dried again. The film obtained was dissolved in dimethylformamide (DMF), and the polymer was precipitated in water. A rubber-like polymer was collected and dried at about 35° C. to about 40° C. under reduced pressure. This procedure was repeated for several times, until a negative test on p-nitrophenol was obtained (see below). Normally it was repeated about 3-4 times. After such a treatment, the yields of coPEURs decreased to ≦80%, however the viscosities increased, which is believed to be the result of the loss of low-molecular-weight fractions.

(C.) Purification of Deprotected Polymers (Polyacids)

After deprotection, polymers were purified by precipitation from an ethanol solution in water. A rubber-like mass was collected and dried at room temperature under reduced pressure.

Example 25

4-AminoTEMPO Attachment and its Biodegradation and Free Radicals Release Study For this study the co-PEA of the following structure was chosen:

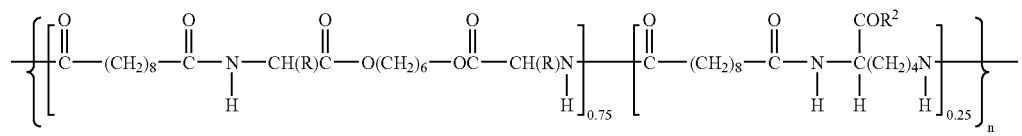

(The hydrogenolysis product of the Example 2) which revealed excellent elasticity (elongation at break ca. 1000%) and was used in in vivo "stent experiments".

4-AminoTEMPO (TAM) was attached to this polyacid using carbonyldiimidazol ($Im_2CO$) as a condensing agent. In typical procedure 1 g of polyacid was dissolved in 10 mL of purified, freshly distilled chloroform. A molar equivalent of carbonyldiimidazole was added at room temperature and stirred. A molar equivalent of TAM was added, stirred for 4 h, and kept at r. t. overnight. The solution was filtered and cast onto a hydrophobic surface. Chloroform was evaporated to dryness. The obtained film was thoroughly washed with distilled water and dried under reduced pressure at r.t. An elastic, light red-brown film was obtained. The degree of TAM attachment was 90-95%, determined by UV spectrophotometry in ethanol solution at 250 nm (Polymer does not absorb at this wavelength).

After TAM attachment, the polymer retained elastic properties. It degraded by lipase according to nearly zero order biodegradation kinetics (that is ideal for drug controlled release devices) while retaining the film's integrity whereas the starting polyacid completely degraded and/or disintegrated within 48 h in slightly alkaline buffer solution in the presence of lipase). TAM attached polymer is designated as GJ-2(TAM).

For the biodegradation study, the film of GJ-2(TAM) was obtained, it was dissolved in 10 mL of chloroform, and a Teflon disk of d=4 cm was covered by this solution for several times and evaporated so that the weight of dried polymeric coating was ca. 500 mg. The disc was placed in a lipase solution (4 mg of the enzyme in 10 mL of phosphate buffer with pH 7.4. 6 mL of the enzyme was dissolved in 15 mL of the buffer—10 mL was used for biodegradation experiment, 5 mL—for the compensation in UV measurements) and placed in thermostat at 37° C. The enzyme solution was changed every 24 h. Every 24 h the film was removed, dried with filer paper and weighed. The buffer solution was analyzed by UV-spectroscopy at 250 nm since the polymeric degradation products don't absorb at this wavelength. The same solution of the enzyme was used for the compensation.

The obtained results indicate that both biodegradation (weight loss) of the polymer and TAM releasing are very close to zero order kinetics.

Since the amide bond through which the TAM is attached to the polymer is rather stable under the biodegradation conditions, it is expected that TAM is released to the polymeric debris. At the same time the calibration curve of TAM in buffer was used for quantitative measurements. Therefore, the amount of TAM (in mg), determined by UV-spectroscopy, corresponds to the free TAM in mg (in mg/equivalent).

After 216 h (9 days) biodegradation polymer lost Ca. 11% of the weight, and ca. 8% of the attached TAM was released This, along with biodegradation and TAM releasing profiles, indicates that the TAM releasing is determined by the erosion of the polymeric film.

Figure 2:
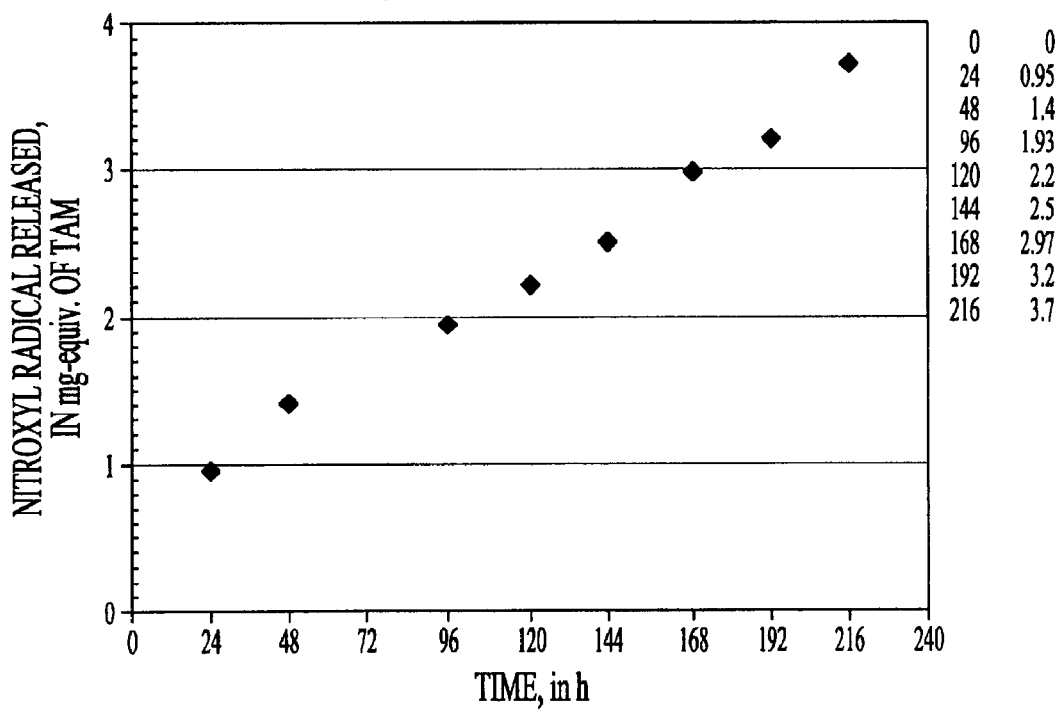
FIG. 2 illustrates the kinetics of nitroxyl radical release from TAM attached to a representative compound, co-PEA, according to an embodiment of the invention.

The results of the biodegradation (weight loss in mg/cm$^2$) of 4-AminoTEMPO (TAM), attached to a co-PEA of the present invention, and the kinetics of nitroxyl radical release from 4-AminoTEMPO (TAM), attached to a co-PEA of the present invention, are shown in the charts below. FIG. 1 illustrates the biodegradation (weight loss in mg/cm$^2$) of 4-Amino TEMPO (TAM) attached to a representative compound of the present invention. FIG. 2 illustrates the kinetics of nitroxyl radical release from 4-Amino TEMPO (TAM) attached to a representative compound of the present invention.

Example 24

Test on Purity (General Procedure)

The coPEA or coPEUR (200-250 mg) was dissolved in a boiling 10% water solution of NaOH (5.0 mL), and the resulting solution was analyzed using UV-VIS spectrophotometer (Specord UV-VIS, Carl Zeiss, Jena, cell of 4 mL, 1=1,0 cm). The absence of the absorption in the region of 250-280 nm (TosO$^-$) and at 430 nm (O$_2$NC$_6$H$_4$O$^-$) indicates that neither p-toluenesulfonic acid nor p-nitrophenol exists in the polymeric sample to any appreciable degree. It is noted that in alkaline media, p-nitrophenol does not absorb in UV region. As such, its absorption does not overlap the absorption of p-toluenesulfonic acid.

The structure of the benzylated polymers prepared in Examples 1-21 is given in the Tables below.

Example 25

TABLE I (VII)

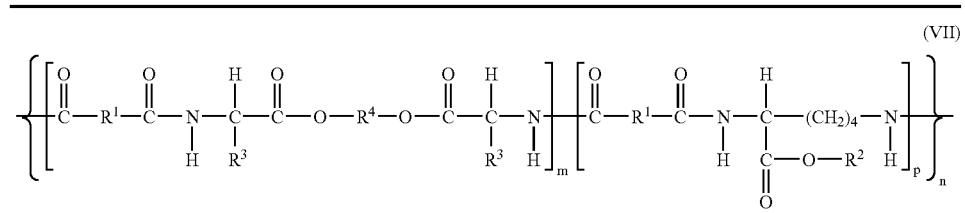

| Compound | R$_1$ | R$_2$ | R$_3$ | R$_4$ | m | p | n |
|---|---|---|---|---|---|---|---|
| (1) | (CH$_2$)$_4$ | Bz | iso-propyl | (CH$_2$)$_6$ | 0.75 | 0.25 | 75 |
| (2) | (CH$_2$)$_8$ | Bz | iso-propyl | (CH$_2$)$_6$ | 0.75 | 0.25 | 65 |
| (3) | (CH$_2$)$_4$ | Bz | iso-propyl and Bz | (CH$_2$)$_6$ | 0.75(0.50 + 0.25) | 0.25 | — |
| (4) | (CH$_2$)$_8$ | Bz | iso-propyl | (CH$_2$)$_6$ | 0.75(0.50 + 0.25) | 0.25 | — |
| (5) | (CH$_2$)$_4$ | Bz | iso-propyl | (CH$_2$)$_6$ | 0.50 | 0.50 | — |
| (6) | (CH$_2$)$_8$ | Bz | iso-propyl | (CH$_2$)$_6$ | 0.50 | 0.50 | — |
| (7) | (CH$_2$)$_4$ | Bz | iso-propyl | (CH$_2$)$_8$ | 0.90 | 0.10 | — |
| (8) | (CH$_2$)$_8$ | Bz | iso-propyl | (CH$_2$)$_4$ | 0.90 | 0.10 | — |
| (9) | (CH$_2$)$_8$ | Bz | iso-propyl | (CH$_2$)$_6$ | 0.90 | 0.10 | — |
| (10) | (CH$_2$)$_8$ | Bz | iso-propyl | (CH$_2$)$_8$ | 0.90 | 0.10 | — |
| (11) | (CH$_2$)$_8$ | Bz | iso-propyl | (CH$_2$)$_{12}$ | 0.90 | 0.10 | — |
| (12) | (CH$_2$)$_{12}$ | Bz | iso-propyl | (CH$_2$)$_6$ | 0.90 | 0.10 | — |

Example 26

TABLE II $$\left\{\left[\begin{array}{c}O\\\|\\-C-O-R^6-O-\overset{O}{\underset{\|}{C}}-\overset{H}{\underset{|}{N}}-\overset{}{\underset{R^3}{C}}-\overset{O}{\underset{\|}{C}}-O-R^4-O-\overset{O}{\underset{\|}{C}}-\overset{H}{\underset{|}{C}}-\overset{}{\underset{R^3}{C}}-\overset{}{\underset{H}{N}}\end{array}\right]_m \left[\begin{array}{c}O\\\|\\-C-O-R^6-O-\overset{O}{\underset{\|}{C}}-\overset{H}{\underset{|}{N}}-\overset{}{\underset{C-OR^2}{\underset{\|}{\underset{O}{C}}}}-(CH_2)_4-\overset{}{\underset{H}{N}}\end{array}\right]_p\right\}_n \quad (XI)$$

| Compound | $R_2$ | $R_3$ | $R_4$ | $R_6$ | m | p | n |
|---|---|---|---|---|---|---|---|
| (13) | Bz | iso-propyl | $(CH_2)_4$ | $(CH_2)_3$ | 0.75 | 0.25 | — |
| (14) | Bz | iso-propyl | $(CH_2)_4$ | $(CH_2)_2-O-(CH_2)_2$ | 0.75 | 0.25 | — |
| (15) | Bz | iso-propyl | $(CH_2)_6$ | $(CH_2)_3$ | 0.75 | 0.25 | 112 |
| (16) | Bz | iso-propyl | $(CH_2)_6$ | $(CH_2)_2-O-(CH_2)_2$ | 0.75 | 0.25 | 130 |
| (17) | Bz | iso-propyl | $(CH_2)_6$ | $(CH_2)_2-O-(CH_2)_2$ | 0.50 | 0.50 | 85 |
| (18) | Bz | iso-propyl | $(CH_2)_6$ | $(CH_2)_2-O-(CH_2)_2$ | 0.90 | 0.10 | 115 |
| (19) | Bz | iso-propyl | $(CH_2)_8$ | $(CH_2)_3$ | 0.75 | 0.25 | — |
| (20) | Bz | iso-propyl | $(CH_2)_8$ | $(CH_2)_2-O-(CH_2)_2$ | 0.75 | 0.25 | — |
| (21) | Bz | iso-propyl | $(CH_2)_8$ | $(CH_2)_2-O-(CH_2)_2$ | 0.90 | 0.10 | — |

The physical properties of the polymers prepared in Examples 1-12 are given in Table III.

Example 27

TABLE III

| Compound | Yield (%) | $\eta_{red}$ (dL/g) | Mw | Mn | Mw/Mn (GPC in THF) | B.W.L. (%)[1] | B.W.L. (%)[2] | B.W.L. (%)[3] | Tg (DSC) |
|---|---|---|---|---|---|---|---|---|---|
| (1) | 90 | 1.30 | 32,100 | 27,000 | 1.19 | | | | |
| (2) | 91 | 1.40 | 31,300 | 21,000 | 1.49 | ~0 | 1-2 | 1-2 | |
| (3) | 94 | 1.40 | | | | ~0 | 10 | 35 | |
| (4) | 95 | 0.77 | | | | | | | 20.6° C. |
| (5) | 93 | 1.25 | | | | | | | |
| (6) | 95 | 1.31 | | | | | | | |
| (7) | 94 | 1.21 | | | | | | | |
| (8) | 95 | 1.28 | | | | | | | |
| (9) | 96 | 1.41 | | | | ~0 | 12 | 38 | |
| (10) | 97 | 1.50 | | | | | | | 27.5° C. |
| (11) | 96 | 0.68 | | | | | | | |
| (12) | 96 | 1.18 | | | | | | | |
| (13) | 63 | 0.32 | | | | | | | |
| (14) | 78 | 0.58 | | | | 4.7[4] | 2.2[5] | 4.4[6] | |
| (15) | 60 | 0.53 | 50,000 | 29,900 | 1.68 | 5.0[7] | 7.3[8] | 8.2[9] | |
| (16) | 68 | 0.72 | 61,900 | 38,500 | 1.61 | 0.4[7] | 5.6[8] | 8.9[9] | |
| (17) | 80 | 0.45 | 37,900 | 22,300 | 1.70 | | | | |
| (18) | 70 | 0.74 | 56,500 | 33,700 | 1.68 | | | | |
| (19) | 84 | 0.46 | | | | 0.9[4] | 2.0[5] | 3.7[6] | |
| (20) | 76 | 0.42 | | | | | | | |
| (21) | 63 | 0.51 | | | | | | | |

[1] B.W.L. (%) is biodegradation (weight loss %) at 37° C. after 120 h in phosphate buffer (pH 7.4).
[2] B.W.L. (%) is biodegradation (weight loss %) at 37° C. after 120 h in phosphate buffer (pH 7.4) with α-chymotrypsin (4 mg/10 mL of buffer).
[3] B.W.L. (%) is biodegradation (weight loss %) at 37° C. after 120 h in phosphate buffer (pH 7.4) with lipase (4 mg/10 mL of buffer).
[4] B.W.L. (%) is biodegradation (weight loss %) at 37° C. after 240 h in phosphate buffer (pH 7.4).
[5] B.W.L. (%) is biodegradation (weight loss %) at 37° C. after 240 h in phosphate buffer (pH 7.4) with α-chymotrypsin (4 mg/10 mL of buffer).
[6] B.W.L. (%) is biodegradation (weight loss %) at 37° C. after 240 h in phosphate buffer (pH 7.4) with lipase (4 mg/10 mL of buffer).
[7] B.W.L. (%) is biodegradation (weight loss %) at 37° C. after 180 h in phosphate buffer (pH 7.4).
[8] B.W.L. (%) is biodegradation (weight loss %) at 37° C. after 180 h in phosphate buffer (pH 7.4) with α-chymotrypsin (4 mg/10 mL of buffer).
[9] B.W.L. (%) is biodegradation (weight loss %) at 37° C. after 180 h in phosphate buffer (pH 7.4) with lipase (4 mg/10 mL of buffer).

The benzylated polymers obtained had high Mw in the range 30,000-60,000 and narrow polydispersity—Mw/Mn=1.2-1.7 (Determined by GPC for the polymers, soluble in THF), and possess excellent film-forming properties. They revealed rather low glass transition temperature (Tg=9-20° C.). The polymers are soluble in common organic solvents like chloroform (all of them), ethanol, (copoly(ester amide)s), ethylacetate (copoly(ester urethane)s), some of them in THF. Both co-PEAs and co-PEURs reveal rather high tendency to in vitro biodegradation. Co-PEAs are more inclined to specific (enzyme catalyzed) hydrolysis, whereas co-PEURs showed the tendency to both specific and non-specific (chemical) hydrolysis.

Example 28

In Vitro Biodegradation Study

In vitro biodegradation studies were performed by weight loss. Standard films with d=4 cm and m=450-550 mg (pure films in case of non-contractive poly(ester amide)s and films on Teflon backing in case of contractive poly(ester urethane)s), were placed into the glass vessels containing 10 mL of 0.2 M phosphate buffer solution with pH=7.4 (either pure buffer or buffer containing 4 mg of an enzyme-α-chymotrypsin or lipase) and placed at 37° C. The films were removed from the solutions after a predetermined time, dried with filter paper and weighted. Buffer or enzyme solution was changed every 24 h.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polymer of formula (VII)

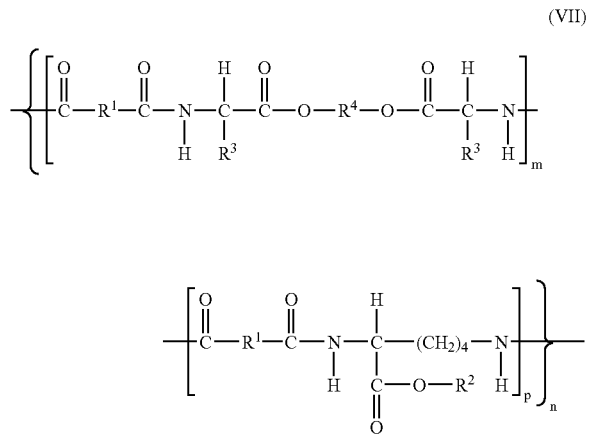

(VII)

wherein
m is about 0.1 to about 0.9;
p is about 0.9 to about 0.1;
n is about 50 to about 150;
each $R^1$ is independently $(C_2$-$C_{20})$alkyl;
each $R^2$ is independently hydrogen, or $(C_6$-$C_{10})$aryl$(C_1$-$C_6)$alkyl;
each $R^3$ is independently hydrogen, $(C_1$-$C_6)$alkyl, $(C_2$-$C_6)$alkenyl, $(C_2$-$C_6)$alkynyl, or $(C_6$-$C_{10})$aryl$(C_1$-$C_6)$alkyl; and
each $R^4$ is independently $(C_2$-$C_{20})$alkyl; that is linked to one or more drugs.

2. The polymer of claim 1 wherein a residue of the polymer is linked directly to a residue of the drug.

3. The polymer of claim 2 wherein the residue of the polymer is linked directly to the residue of the drug through an amide, ester, ether, amino, ketone, thioether, sulfinyl, sulfonyl, disulfide, or a direct linkage.

4. The polymer of claim 2 wherein the residue of the polymer is linked directly to the residue of the drug through one of the following linkages: —N(R)C(=O)—, —C(=O)N(R)—, —OC(=O)—, —C(=O)O—, —O—, —C(=O)—, —S—, —S(O)—, —S(O)$_2$—, —S—S—, —N(R)—, or C—C; wherein each R is independently H or $(C_1$-$C_6)$alkyl.

5. The polymer of claim 1 wherein a residue of the polymer is linked to a residue of the drug, through a linker.

6. The polymer of claim 5 wherein the linker separates the residue of the polymer and the residue of the drug by about 5 angstroms to about 200 angstroms, inclusive, in length.

7. The polymer of claim 5 wherein (1) the residue of the polymer is linked to the linker and (2) the linker is linked to the residue of the drug, independently, through an amide, ester, ether, amino, ketone, thioether, sulfinyl, sulfonyl, disulfide, or a direct linkage.

8. The polymer of claim 5 wherein (1) the residue of the polymer is linked to the linker and (2) the linker is linked to the residue of the drug, independently, through one of the following linkages: —N(R)C(=O)—, —C(=O)N(R)—, —OC(=O)—, —C(=O)O—, —O—, —C(=O)—, —S—, —S(O)—, —S(O)$_2$—, —S—S—, —N(R)—, or C—C; wherein each R is independently H or $(C_1$-$C_6)$alkyl.

9. The polymer of claim 5 wherein the linker is a divalent radical of the formula W-A-Q wherein A is $(C_1$-$C_{24})$alkyl, $(C_2$-$C_{24})$alkenyl, $(C_2$-$C_{24})$alkynyl, $(C_3$-$C_8)$cycloalkyl, or $(C_6$-$C_{10})$ aryl, wherein W and Q are each independently —N(R)C(=O)—, —C(=O)N(R)—, —OC(=O)—, —C(=O)O—, —O—, —S—, —S(O)—, —S(O)$_2$—, —S—S—, —N(R)—, —C(=O)—, or a direct bond; wherein each R is independently H or $(C_1$-$C_6)$alkyl.

10. The polymer of claim 5 wherein the linker is an αω-divalent radical formed from a peptide or an amino acid.

11. The polymer of claim 10 wherein the peptide comprises 2 to about 25 amino acids.

12. The polymer of claim 10 wherein the peptide is poly-L-lysine, poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-arginine, or poly-L-lysine-L-tyrosine.

13. The polymer of claim 1 wherein the one or more drugs are each independently: a polynucleotide, polypeptide, oligonucleotide, gene therapy agent, nucleotide analog, nucleoside analog, polynucleic acid decoy, therapeutic antibody, abciximab, anti-inflammatory agent, blood modifier, anti-platelet agent, anti-coagulation agent, immune suppressive agent, anti-neoplastic agent, anti-cancer agent, anti-cell proliferation agent, or nitric oxide releasing agent.

14. A formulation comprising a polymer of formula (VII)

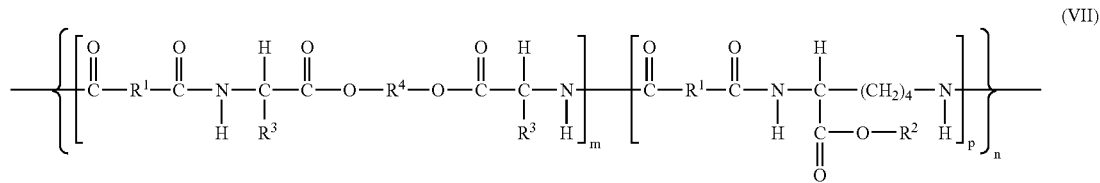

wherein
- m is about 0.1 to about 0.9;
- p is about 0.9 to about 0.1;
- n is about 50 to about 150;
- each $R^1$ is independently $(C_2-C_{20})$alkyl;
- each $R^2$ is independently hydrogen, or $(C_6-C_{10})$aryl$(C_1-C_6)$alkyl;
- each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl; and
- each $R_4$ is independently $(C_2C_{20})$alkyl; and one or more drugs.

15. The formulation of claim 14 wherein the one or more drugs are each independently: a polynucleotide, polypeptide, oligonucleotide, gene therapy agent, nucleotide analog, nucleoside analog, polynucleic acid decoy, therapeutic antibody, abciximab, anti-inflammatory agent, blood modifier, anti-platelet agent, anti-coagulation agent, immune suppressive agent, anti-neoplastic agent, anti-cancer agent, anti-cell proliferation agent, or nitric oxide releasing agent.

16. A polymer of formula (XI)

18. The polymer of claim 17 wherein the residue of the polymer is linked directly to the residue of the drug through an amide, ester, ether, amino, ketone, thioether, sulfinyl, sulfonyl, disulfide, or a direct linkage.

19. The polymer of claim 16 wherein the residue of the polymer is linked directly to the residue of the drug through one of the following linkages: —N(R)C(=O)—, —C(=O)N(R)—, —OC(=O)—, —C(=O)O—, —O—, —C(=O)—, —S—, —S(O)—, —S(O)$_2$—, —S—S—, —N(R)—, or C—C; wherein each R is independently H or $(C_1-C_6)$alkyl.

20. The polymer of claim 16 wherein a residue of the polymer is linked to a residue of the drug, through a linker.

21. The polymer of claim 20 wherein the linker separates the residue of the polymer and the residue of the drug by about 5 angstroms to about 200 angstroms, inclusive, in length.

22. The polymer of claim 20 wherein (1) the residue of the polymer is linked to the linker and (2) the linker is linked to

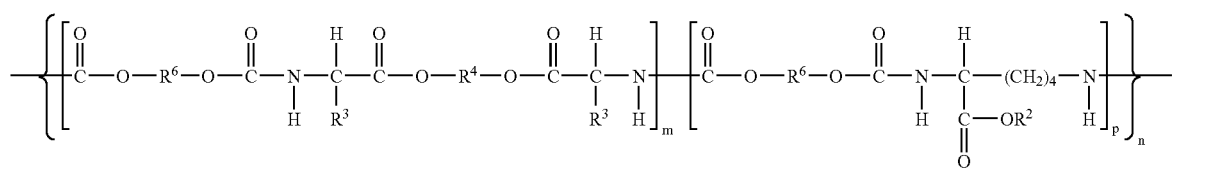

wherein
- m is about 0.1 to about 0.9;
- p is about 0.9 to about 0.1;
- n is about 50 to about 150;
- each $R^2$ is independently hydrogen, or $(C_6-C_{10})$aryl$(C_1-C_6)$alkyl;
- each $R^3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl;
- each $R^4$ is independently $(C_2-C_{20})$alkyl; and
- each $R^6$ is independently $(C_2-C_{20})$alkyl or $(C_2-C_8)$alkyloxy$(C_2-C_{20})$alkyl; that is linked to one or more drugs.

17. The polymer of claim 16 wherein a residue of the polymer is linked directly to a residue of the drug.

the residue of the drug, independently, through an amide, ester, ether, amino, ketone, thioether, sulfinyl, sulfonyl, disulfide, or a direct linkage.

23. The polymer of claim 20 wherein (1) the residue of the polymer is linked to the linker and (2) the linker is linked to the residue of the drug, independently, through one of the following linkages: —N(R)C(=O)—, —C(=O)N(R)—, —OC(=O)—, —C(=O)O—, —O—, —C(=O)—, —S—, —S(O)—, —S(O)$_2$—, —S—S—, —N(R)—, or C—C; wherein each R is independently H or $(C_1-C_6)$alkyl.

24. The polymer of claim 20 wherein the linker is a divalent radical of the formula W-A-Q wherein A is $(C_1-C_{24})$alkyl, $(C_2-C_{24})$alkenyl, $(C_2-C_{24})$alkynyl, $(C_3-C_8)$cycloalkyl, or $(C_6-C_{10})$aryl, wherein W and Q are each independently —N(R)C(=O)—, —C(=O)N(R)—, —OC(=O)—, —C(=O)O—, —O—, —S—, —S(O)—, —S(O)$_2$—, —S—S—, —N(R)—, —C(=O)—, or a direct bond; wherein each R is independently H or $(C_1-C_6)$alkyl.

25. The polymer of claim 20 wherein the linker is a 1,107-divalent radical formed from a peptide or an amino acid.

26. The polymer of claim 25 wherein the peptide comprises 2 to about 25 amino acids.

27. The polymer of claim 25 wherein the peptide is poly-L-lysine, poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-arginine, or poly-L-lysine-L-tyrosine.

28. The polymer of claim 16 wherein the one or more drugs are each independently: a polynucleotide, polypeptide, oligonucleotide, gene therapy agent, nucleotide analog, nucleoside analog, polynucleic acid decoy, therapeutic antibody, abciximab, anti-inflammatory agent, blood modifier, anti-platelet agent, anti-coagulation agent, immune suppressive agent, anti-neoplastic agent, anti-cancer agent, anti-cell proliferation agent, or nitric oxide releasing agent.

29. A formulation comprising a polymer of formula (XI)

33. The polymer of claim 1 wherein each $R^3$ is independently iso-butyl or benzyl.

34. The polymer of claim 1 wherein each $R^4$ is independently $(CH_2)_4$, $(CH_2)_6$, $(CH_2)_8$, or $(CH_2)_{12}$.

35. The polymer of claim 1 wherein p/(p+m) is about 0.9 to about 0.1.

36. The polymer of claim 1 wherein m/(p+m) is about 0.1 to about 0.9.

37. The polymer of claim 16 wherein each $R^2$ is independently hydrogen or benzyl.

38. The polymer of claim 16 wherein each $R^3$ is independently iso-butyl or benzyl.

39. The polymer of claim 16 wherein each $R^4$ is independently $(CH_2)_4$, $(CH_2)_6$, $(CH_2)_8$, or $(CH_2)_{12}$.

40. The polymer of claim 16 wherein each $R^6$ is independently $(CH_2)_3$ or $(CH_2)_2$—O—$(CH_2)_2$.

41. The polymer of claim 16 wherein p/(p+m) is about 0.9 to about 0.1.

42. The polymer of claim 16 wherein m/(p+m) is about 0.1 to about 0.9.

43. The formulation of claim 14 wherein each $R^1$ is independently $(CH_2)_4$, $(CH_2)_8$, or $(CH_2)_{12}$.

44. The formulation of claim 14 wherein each $R^2$ is independently hydrogen or benzyl.

(XI)

$$\left\{ \left[ \begin{array}{c} O \\ \| \\ C \end{array} -O-R^6-O- \begin{array}{c} O \\ \| \\ C \end{array} -N- \begin{array}{c} H \\ | \\ C \\ | \\ H \end{array} \begin{array}{c} \\ | \\ R^3 \end{array} \begin{array}{c} O \\ \| \\ C \end{array} -O-R^4-O- \begin{array}{c} O \\ \| \\ C \end{array} - \begin{array}{c} H \\ | \\ C \\ | \\ R^3 \end{array} -N- \right]_m \left[ \begin{array}{c} O \\ \| \\ C \end{array} -O-R^6-O- \begin{array}{c} O \\ \| \\ C \end{array} -N- \begin{array}{c} H \\ | \\ C \\ | \\ C=O \\ | \\ OR^2 \end{array} -(CH_2)_4- \begin{array}{c} H \\ | \\ N \\ | \\ H \end{array} \right]_p \right\}_n$$

wherein
  m is about 0.1 to about 0.9;
  p is about 0.9 to about 0.1;
  n is about 50 to about 150;
  each $R^2$ is independently hydrogen, or $(C_6-C_{10})$aryl$(C_1-C_6)$alkyl;
  each $R_3$ is independently hydrogen, $(C_1-C_6)$alkyl, $(C_2-C_6)$alkenyl, $(C_2-C_6)$alkynyl, or $(C_6-C_{10})$aryl$(C_1-C_6)$alkyl;
  each $R^4$ is independently $(C_2-C_{20})$alkyl; and
  each $R^6$ is independently $(C_2-C_{20})$alkyl or $(C_2-C_8)$alkyloxy$(C_2-C_{20})$alkyl; and one or more drugs.

30. The formulation of claim 29 wherein the one or more drugs are each independently: a polynucleotide, polypeptide, oligonucleotide, gene therapy agent, nucleotide analog, nucleoside analog, polynucleic acid decoy, therapeutic antibody, abciximab, anti-inflammatory agent, blood modifier, anti-platelet agent, anti-coagulation agent, immune suppressive agent, anti-neoplastic agent, anti-cancer agent, anti-cell proliferation agent, or nitric oxide releasing agent.

31. The polymer of claim 1 wherein each $R^1$ is independently $(CH_2)_4$, $(CH_2)_8$, or $(CH_2)_{12}$.

32. The polymer of claim 1 wherein each $R^2$ is independently hydrogen or benzyl.

45. The formulation of claim 14 wherein each $R^3$ is independently iso-butyl or benzyl.

46. The formulation of claim 14 wherein each $R^4$ is independently $(CH_2)_4$, $(CH_2)_6$, $(CH_2)_8$, or $(CH_2)_{12}$.

47. The formulation of claim 14 wherein p/(p+m) is about 0.9 to about 0.1.

48. The formulation of claim 14 wherein m/(p+m) is about 0.1 to about 0.9.

49. The formulation of claim 29 wherein each $R^2$ is independently hydrogen or benzyl.

50. The formulation of claim 29 wherein each $R^3$ is independently iso-butyl or benzyl.

51. The formulation of claim 29 wherein each $R^4$ is independently $(CH_2)_4$, $(CH_2)_6$, $(CH_2)_8$, or $(CH_2)_{12}$.

52. The formulation of claim 29 wherein each $R^6$ is independently $(CH_2)_3$ or $(CH_2)_2$—O—$(CH_2)_2$.

53. The formulation of claim 29 wherein p/(p+m) is about 0.9 to about 0.1.

54. The formulation of claim 29 wherein m/(p+m) is about 0.1 to about 0.9.

* * * * *

UNITED STATES PATENT AND TRADEMARK OFFICE
CERTIFICATE OF CORRECTION

PATENT NO. : 7,304,122 B2 Page 1 of 1
APPLICATION NO. : 10/362848
DATED : December 4, 2007
INVENTOR(S) : Chu et al.

It is certified that error appears in the above-identified patent and that said Letters Patent is hereby corrected as shown below:

On the face page, in "Assistant Examiner", in column 2, line 1, delete "Gennadly" and insert -- Gennadiy --, therefor.

Column 50, line 50, in Claim 10, delete "αω" and insert -- α,ω --, therefor.

Column 51, line 27, in Claim 14, delete "$R_4$" and insert -- $R^4$ --, therefor.

Column 51, line 27, in Claim 14, delete "$(C_2C_{20})$" and insert -- $(C_2-C_{20})$ --, therefor.

Column 53, line 6 (Approx.), in Claim 25, after "1," delete "107" and insert -- ω --, therefor.

Column 53, line 50, in Claim 29, delete "$R_3$" and insert -- $R^3$ --, therefor.

Column 54, line 57, in Claim 51, delete "$(CH_{2)12}$." and insert -- $(CH_2)_{12}$. --, therefor.

Signed and Sealed this

Fifteenth Day of April, 2008

JON W. DUDAS
*Director of the United States Patent and Trademark Office*